United States Patent
Anthony et al.

(10) Patent No.: US 10,016,518 B2
(45) Date of Patent: Jul. 10, 2018

(54) INFLAMMATION IMAGING AND THERAPY

(71) Applicant: Isis Innovation Limited, Oxford (GB)

(72) Inventors: Daniel Anthony, Oxford (GB);
Benjamin Guy Davis, Oxford (GB);
Guillaume Bort, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 353 days.

(21) Appl. No.: 14/421,943

(22) PCT Filed: Aug. 15, 2013

(86) PCT No.: PCT/GB2013/052173
§ 371 (c)(1),
(2) Date: Feb. 16, 2015

(87) PCT Pub. No.: WO2014/027203
PCT Pub. Date: Feb. 20, 2014

(65) Prior Publication Data
US 2015/0231281 A1    Aug. 20, 2015

(30) Foreign Application Priority Data
Aug. 17, 2012   (GB) .................................. 1214736.9

(51) Int. Cl.
| | | |
|---|---|---|
| A61B 5/055 | (2006.01) | |
| A61K 49/10 | (2006.01) | |
| C07H 23/00 | (2006.01) | |
| A61K 31/702 | (2006.01) | |

(52) U.S. Cl.
CPC ............ *A61K 49/10* (2013.01); *A61K 31/702* (2013.01); *C07H 23/00* (2013.01); *A61K 49/101* (2013.01)

(58) Field of Classification Search
None
See application file for complete search history.

(56) References Cited

U.S. PATENT DOCUMENTS

| | | | |
|---|---|---|---|
| 2007/0265170 A1 | 11/2007 | Blixt et al. | |
| 2012/0107838 A1* | 5/2012 | Grainger .............. | G01N 33/574 435/7.23 |

FOREIGN PATENT DOCUMENTS

| | | |
|---|---|---|
| JP | 2009096749 A | 5/2009 |
| WO | 9728173 A1 | 8/1997 |
| WO | 9728174 A1 | 8/1997 |
| WO | 2007020450 A3 | 2/2007 |

OTHER PUBLICATIONS

Cipolla et al. (Curr. Med. Chem. 2011, 18, 1002-1018).*
Eklind et al: Large-Scale synthesis of a Lewis B tetrasaccharide derivative; Journal of Carbohydrate Chemistry, 1996(9), 1161-1178.
Todoroki et al; Rhodamin B amine as a highly sensitive: Journal of Chromatography A, 2004, vol. 1038, issue 1-2, 113-120.
Wilson et al; Ultraviolet Photodissociation at 355cm of Fluorescently labelled Oligosaccharides; Analytical Chemistry, 2008, 80(13), 5186-5196.
Leo et al; Improved determination of milk oligosaccharides..; Journal of Chromatography A, 2009, 1216(9), 1520-1523.
Bekiroglu et al; Hydroxy protons in conformational study of a Lewis b tetrasaccharide derivative; Carbohydrate Research, 2000, 328(3), 409-418.
Fourniere et al; Synthesis of the Lewis b pentasaccharide and a HSA-conjugate thereof; Tetrahedron, 2010, 66(3), 7850-7855.
Weikkolainen et al; Conjugation of oligosaccharide by reductive animation to amine modified chondroitin oligomer . . . ; Glycoconjugate Journal 2007, 24(2/3), 157-165.
Haselhorst, Thomas et al: Molecular Recognition of Sialyl Lewis x and Related Saccharides by Two Lectins; JACS vol. 123, No. 43, 2001, pp. 10705-10714.
Zemlyanukhina, T.V. et al: Selectin receptors: preparation of spacer-armed sulfated trisaccharides Lewis A and Lewis X and neoglycoconjugates thereof; Carbohydrate Letters, vol. 1 No. 4, 1995, p. 279.
Eisele, T. et al: Synthesis of a thio-linked Lewis A (Le) epitope; Carbohydrate Research, vol. 306, No. 1-2, 1998, pp. 81-91.
Junmin Zhu et al: Biomimetic Glycoliposomes as Nanocarriers for Targeting P-Selectin on Activated Platelets; Bioconjugate Chemistry, vol. 18, No. 5, 2007, pp. 1366-1369.
Gimi, Barjor et Al: Noninvasive MRI of Endothelial Cell Response to Human Breast Cancer Cells; Neoplasia, vol. 8, No. 3, 2006.
Takada, A. et al: Contribution of Carbohydrate Antigens Sialyl Lewis A and Sialyl Lewis X to Adhesion of Human Cancer Cells to Vascular Enothelium; Cancer Research, vol. 53, 1993, pp. 354-361.

* cited by examiner

*Primary Examiner* — Michael G Hartley
*Assistant Examiner* — Melissa J Perreira
(74) *Attorney, Agent, or Firm* — Quarles & Brady LLP

(57) ABSTRACT

An imaging agent comprising a conjugate of an oligosaccharide moiety with an imaging moiety. The oligosaccharide is Lewis A or Lewis B or a mimetic thereof, or a pharmaceutically acceptable salt or PEGylated form of Lewis A or Lewis B or its mimetics. Lewis A and Lewis B and its mimetics are also provided for use in the therapeutic treatment of inflammatory diseases, autoimmune diseases and cancer.

13 Claims, 1 Drawing Sheet

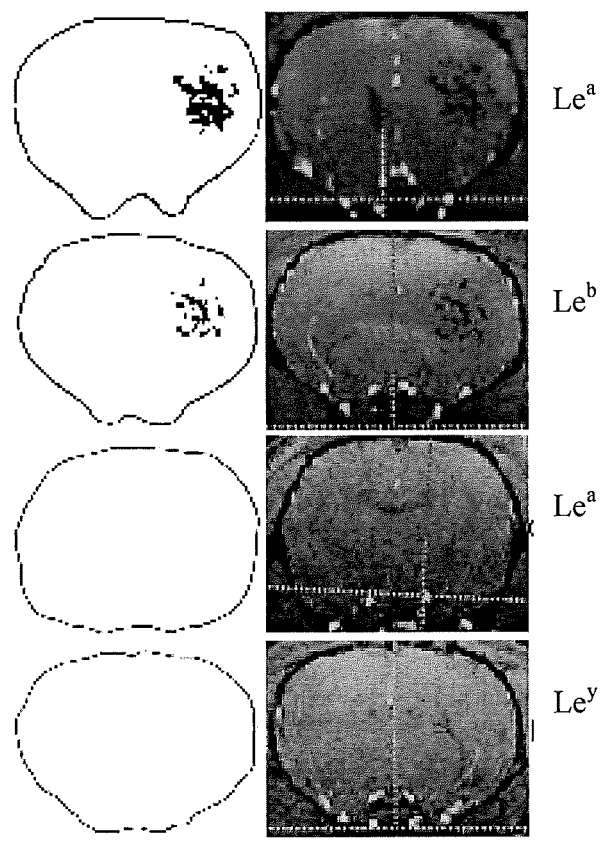

INFLAMMATION IMAGING AND THERAPY

FIELD OF THE INVENTION

This invention relates to imaging agents which comprise a conjugate of an oligosaccharide with an imaging moiety. The agents of the invention can be used in a variety of imaging techniques including magnetic resonance imaging, positron emission tomography (PET), single-photon-emission-computed tomography (SPECT) and fluorescence imaging. The invention also relates to the use of Lewis A or Lewis B sugars, or their mimetics, in therapeutic treatments.

BACKGROUND TO THE INVENTION

A variety of imaging techniques are available for diagnostic purposes. Such imaging techniques are generally non invasive and include magnetic resonance imaging (MRI) and ultrasound. Contrast agents are used in imaging to increase the signal difference between the area of interest and background. Such agents can be divided into two general categories, those passive agents which non-specifically enhance the signal that is produced and targeted contrast agents which are chemically modified in order to localise to a specific cell type or tissue through an active mechanism.

Targeted contrast agents that can be localised to a particular cell or tissue type can potentially allow the non-invasive visualisation of a variety of disease states. Such targeted agents need to overcome the difficulties of high background signal in order to provide a clear picture for the clinician. There is a need for improved contrast agents that can be targeted to cell surface receptors to enhance imaging techniques.

SUMMARY OF THE INVENTION

The present inventors have surprisingly found that the Lewis A (hereinafter $Le^a$) and Lewis B (hereinafter $Le^b$) sugars and mimetics of these sugars recognise and bind to activated endothelial cells in vivo. Furthermore, when conjugated to a suitable imaging moiety, such as an MRI/PET/SPECT visable imaging moiety, the conjugate enables the activated endothelium to be visualised. The conspicuity of these conjugates is significantly improved compared with known passive or targeted imaging agents. Accordingly, the present invention provides an imaging agent comprising a conjugate of an oligosaccharide with an imaging moiety, wherein the oligosaccharide is Lewis A or Lewis B or a mimetic thereof, or a pharmaceutically acceptable salt or PEGylated form of Lewis A or Lewis B or a Lewis A or B mimetic:

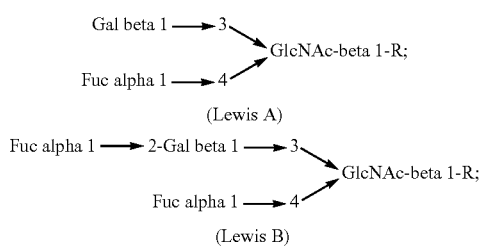

(Lewis A)

(Lewis B)

wherein R represents the point of attachment to the imaging moiety.

In particular, the present invention provides an imaging agent comprising a conjugate of an oligosaccharide with an imaging moiety, wherein the oligosaccharide is of formula (I) or a pharmaceutically acceptable salt or PEGylated form thereof:

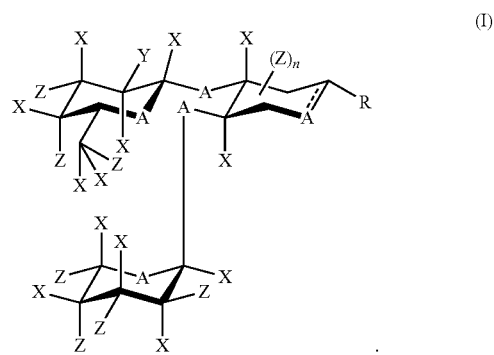

(I)

wherein each Z is the same or different and is selected from OH, hydrogen, halogen, $C_{1-6}$alkoxy, —NR'R", —NR'COR", —N(COR')(COR"), —SR', —COR', —COOR', —OC(O)R', —OC(O)OR', —OC(O)NR'R", —OC(O)SR', —OP(O)(OR')(OR"), —OSO$_3$H, or $C_{1-12}$ alkyl, $C_{2-12}$ alkenyl or $C_{2-12}$ alkynyl, which is optionally substituted with one or more substituents selected from halogen, NH$_2$, N$_3$, CN, COOH, COO($C_{1-4}$ alkyl), OH and $C_{1-4}$ alkoxy;

each X is the same or different and is selected from OH, hydrogen, halogen, $C_{1-6}$alkoxy, —NR'R", —NR'COR", —N(COR')(COR"), —SR', —COR', —COOR', —OC(O)R', —OC(O)OR', —OC(O)NR'R", —OC(O)SR', —OP(O)(OR')(OR"), —OSO$_3$H, or $C_{1-12}$ alkyl, $C_{2-12}$ alkenyl or $C_{2-12}$ alkynyl, which is optionally substituted with one or more substituents selected from halogen, NH$_2$, N$_3$, CN, COOH, COO($C_{1-4}$ alkyl), OH and $C_{1-4}$ alkoxy; each A is the same or different and is selected from CR'R", O, S and NR';

n is 0, 1, 2, 3 or 4;

Y is either a group Z as defined above or a saccharide unit of formula (II):

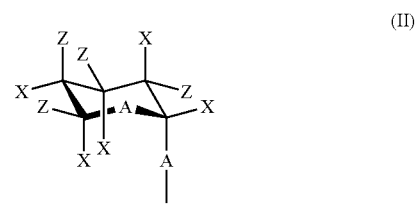

(II)

wherein X, Z and A are as defined above;
R represents the point of attachment to the imaging moiety; and
R' and R" are identical or different and are selected from hydrogen and $C_{1-12}$ alkyl groups which are optionally substituted with one or more substituents selected from halogen, NH$_2$, N$_3$, CN, COOH, COO($C_{1-4}$ alkyl), OH and $C_{1-4}$ alkoxy.

Also provided is an imaging method comprising carrying out medical imaging on a subject, wherein an imaging agent is present in the blood stream of the subject. The imaging method of the invention in one embodiment comprises the steps of i) administering to a subject an imaging agent of the invention; and
ii) carrying out medical imaging on the subject.

The ability of Le$^a$ and Le$^b$ and their mimetics to bind to the activated endothelium also confirms the use of these sugars in blocking interactions of cells circulating in the blood with the activated endothelium, and thus suppressing associated disease processes. Accordingly, these sugars can be used in therapeutic treatments of inflammatory diseases (osteoarthritis, burns, spinal cord injury, stroke, ischeamic heart disease, atherosclerosis), autoimmune diseases (multiple sclerosis, rheumatoid arthritis, inflammatory bowel disease, graft versus host disease, etc) and cancer (including metastasis).

The present invention therefore also provides a compound which is an oligosaccharide of formula (III) or a salt thereof or a PEGylated form thereof:

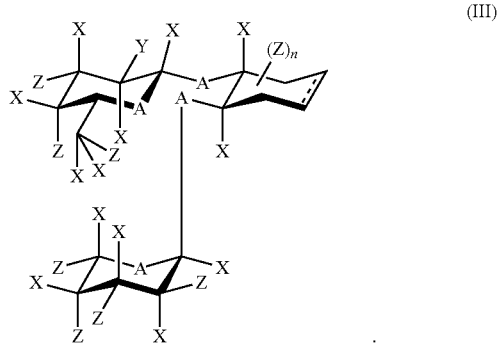
(III)

wherein X, Y, Z, n and A are as defined above, or a pharmaceutically acceptable composition comprising the compound together with a pharmaceutically acceptable carrier or diluent, for use in the treatment of an inflammatory disease, an autoimmune disease or cancer. Also provided is a method for the treatment of an inflammatory disease, an autoimmune disease or cancer, which method comprises administering to a subject an effective amount of a compound or composition as defined above. Also provided is the use of a compound or composition as defined above in the manufacture of a medicament for the treatment of an inflammatory disease, an autoimmune disease or cancer.

BRIEF DESCRIPTION OF THE FIGURES

FIG. 1 provides images obtained in accordance with Example 3, comparing imaging agents comprising Lewis A and Lewis B according to the invention with an imaging agent comprising Lewis Y.

DETAILED DESCRIPTION OF THE INVENTION

As used herein, an alkyl group or moiety is a linear or branched alkyl group or moiety containing from 1 to 12, preferably from 1 to 8, for example from 1 to 6, carbon atoms such as a $C_{1-4}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, an alkenyl group or moiety is a linear or branched alkenyl group or moiety containing from 2 to 12, preferably from 2 to 8, for example from 2 to 6, carbon atoms such as a $C_{2-4}$ alkenyl group or moiety. Examples of $C_{2-4}$ alkenyl groups and moieties include ethenyl, propenyl, and butenyl. For the avoidance of doubt, where two alkenyl moieties are present in a group, the alkenyl moieties may be the same or different.

As used herein, an alkynyl group or moiety is a linear or branched alkynyl group or moiety containing from 2 to 12, preferably from 2 to 8, for example from 2 to 6, carbon atoms such as a $C_{2-4}$ alkynyl group or moiety. Examples of $C_{2-4}$ alkynyl groups and moieties include ethynyl, propynyl and butynyl. For the avoidance of doubt, where two alkynyl moieties are present in a group, the alkynyl moieties may be the same or different.

An alkyl, alkenyl or alkynyl group as used herein may be unsubstituted or substituted. For example it may be substituted with up to four, for example one, two or three, substituents selected from halogen, $NH_2$, $N_3$, CN, COOH, COO($C_{1-4}$ alkyl), OH and $C_{1-4}$ alkoxy. Preferred substituents are halogen, $NH_2$, OH and $C_{1-2}$alkoxy. The substituents are themselves unsubstituted. Typically, an alkyl, alkenyl or alkynyl group as used herein is unsubstituted or substituted with one substituent. Preferably it is unsubstituted.

As used herein the term amino represents a group of formula —$NH_2$. The term $C_{1-2}$ alkylamino represents a group of formula —NHR' wherein R' is methyl or ethyl. The term alkyl)amino represents a group of formula —NR'R" wherein R' and R" are the same or different and represent methyl or ethyl. As used herein a $C_{1-2}$ acetylamino group is a $C_{1-2}$ acetyl group attached to an amino group as defined above. Similarly, a di($C_{1-2}$)acetylamino group is an amino group bearing two $C_{1-2}$ acetyl groups.

As used herein, an alkoxy group is typically a said alkyl group attached to an oxygen atom. Similarly, an alkylthio group is typically a said alkyl group attached to a thio group.

A used herein halogen is typically fluorine, chlorine, bromine or iodine, preferably fluorine or chlorine, most preferably fluorine.

The conjugates of the invention comprise an oligosaccharide moiety and an imaging moiety. An imaging moiety may be bound to two or more oligosaccharide moieties, in which case the oligosaccharide moieties may be the same or different. Preferably, the oligosaccharide moiety is Le$^a$ or Le$^b$, most preferably Le$^a$. Where the oligosaccharide moiety is Le$^a$ or Le$^b$, it can be represented as follows:

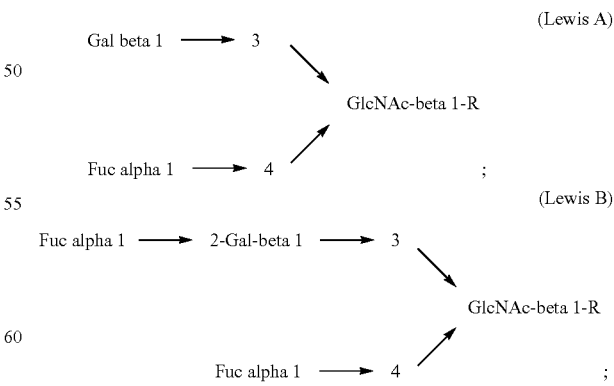

wherein R represents the point of attachment to the imaging agent.

Mimetics of Le$^a$ and Le$^b$ can also be used. Typically, the mimetics will contain one or more modifications compared with the basic oligosaccharide structures. For example, the mimetic may contain one, two, three or four modifications compared with the basic oligosaccharide structure. Typically, each saccharide unit within the $Le^a$ or $Le^b$ unit contains none, one or two, preferably none or one modification.

Where an OH or NAc group on the $Le^a$ or $Le^b$ oligosaccharide is modified, preferred modifications include replacement of the OH or NAc group with hydrogen, halogen, $C_{1-6}$ alkoxy, —NR'R", —NR'COR", —N(COR')(COR"), —SR', —COOR', —OP(O)(OR')(OR"), or $C_{1-6}$ alkyl which is optionally substituted with one or two substituents selected from halogen, $NH_2$, OH and $C_{1-2}$alkoxy, wherein R' and R" are identical or different and are selected from hydrogen and $C_{1-6}$ alkyl groups which are optionally substituted with one or two substituents selected from halogen, $NH_2$, OH and $C_{1-2}$ alkoxy. An NAc group may alternatively be replaced with OH. Particularly preferred modifications include replacement of the OH or NAc group with hydrogen, halogen, methoxy, ethoxy, —$NH_2$, ($C_{1-2}$alkyl)amine, di($C_{1-2}$ alkyl)amine, ($C_{1-2}$acetyl)amine, di($C_{1-2}$acetyl)amine, mercapto, methylthio, ethylthio or —OP(O)(OH)$_2$, or replacement of NAc with OH. Typically, none, one, two or three, preferably none or one, OH or NAc groups in the $Le^a$ or $Le^b$ oligosaccharide are modified.

Where a hydrogen atom on the $Le^a$ or $Le^b$ oligosaccharide is modified, preferred modifications include replacement of the hydrogen atom with a halogen, e.g. fluorine.

An alternative modification is the reversal of the axial and equatorial positions on one or more, for example one, carbon atom within the saccharide unit, thus replacement of a hydrogen atom with OH and simultaneous replacement of the OH carried on the same carbon atom with H. If desired, the hydrogen atom may alternatively be replaced with one of the modifications described above for OH groups.

The modifications to hydrogen and OH groups may be made to groups carried on a single carbon atom, resulting in a disubstituted carbon atom. Alternatively, the modifications may be made on different carbon atoms. Where a carbon atom is disubstituted, the OH group is typically modified as described above and the hydrogen atom is typically replaced with OH, halogen, methoxy, ethoxy, —$NH_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio or —OP(O)(OH)$_2$.

Typically, none, one, two or three, preferably none or one, hydrogen atoms in the $Le^a$ or $Le^b$ oligosaccharide are modified.

Where an —O— moiety on the $Le^a$ or $Le^b$ oligosaccharide is modified, preferred modifications include replacement of the —O— moiety with —SH—, —NH— or —N($C_{1-6}$)alkyl, typically with —SH—, —NH— or —N(Me)-. Typically, none, one, two or three, preferably none or one, —O— groups in the $Le^a$ or $Le^b$ oligosaccharide are modified.

Thus, preferred $Le^a$ and $Le^b$ mimetics are those wherein one, two or three, typically one of the following modifications is made:
(i) one or more OH and/or NAc groups are independently replaced with hydrogen, halogen, methoxy, ethoxy, —$NH_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio or —OP(O)(OH)$_2$, or in the case of NAc replaced with OH;
(ii) one or more hydrogen atoms are independently replaced with fluorine;
(iia) the axial and equatorial positions on one or more carbon atoms are reversed;
(iib) one or more carbon atoms are disubstituted such that both the OH and hydrogen are replaced with a group which is independently selected from halogen, methoxy, ethoxy, —$NH_2$, ($C_{1-2}$alkyl)amine, di($C_{1-2}$alkyl)amine, ($C_{1-2}$acetyl) amine, di($C_{1-2}$acetyl)amine, mercapto, methylthio, ethylthio or —OP(O)(OH)$_2$;
(iii) one or more —O— moieties are independently replaced with —SH—, —NH— or —N(Me)-;
(iv) in the Glc saccharide unit, the unit —$C_1$(R)—O— is replaced with —$C_1$(R)=N—.

In a further preferred embodiment, the $Le^a$ or $Le^b$ mimetic contains one, two or three modifications (i); and/or one, two or three modifications (ii); and/or one, two or three modifications (iia); and/or one, two or three modifications (iib); and/or one modification (iii); and/or one modification (v).

Typically, the mimetic of $Le^a$ or $Le^b$ contains a modification (i) and/or modifications (ii).

The structure of $Le^a$ and $Le^b$ and their mimetics can alternatively be described with reference to formula (I). In formula (I), Y may either represent a group Z (corresponding to $Le^a$ and its mimetics) or a saccharide unit of formula (II) (corresponding to $Le^b$ and its mimetics). Thus, the compounds of formula (I) can alternatively be depicted as compounds of either formula (Ia) or (Ib):

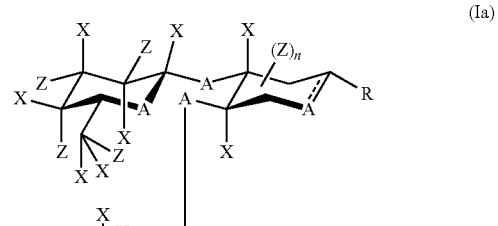

(Ia)

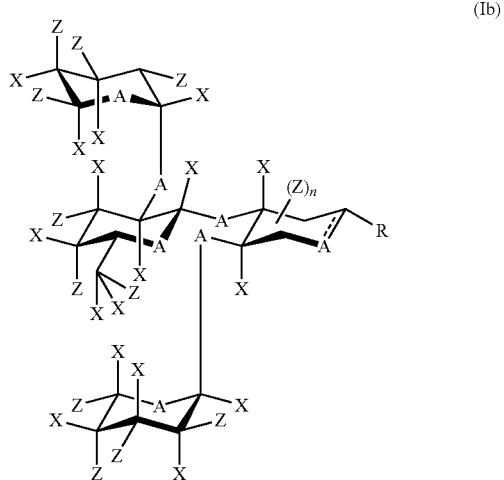

(Ib)

wherein Z, X, n, A and R are as defined for formula (I). For the avoidance of doubt, in formula (Ib) where groups Z, A and X are present on the additional saccharide unit, any group Z within formula (Ib) may be the same or different. Similarly, any group A within formula (Ib) may be the same or different. Further, any group X within formula (Ib) may be the same or different.

In formula (I), (Ia) or (Ib), typically Z is OH, hydrogen, halogen, $C_{1-6}$ alkoxy, —NR'COR", —N(COR')(COR"), —SR', —COOR', —OP(O)(OR')(OR"), or $C_{1-6}$ alkyl which is optionally substituted with one or two substituents selected from halogen, $NH_2$, OH and $C_{1-2}$ alkoxy, wherein R' and R" are identical or different and are selected from hydrogen and $C_{1-6}$ alkyl groups which are optionally substituted with one or two substituents selected from halogen, $NH_2$, OH and $C_{1-2}$ alkoxy. Particularly preferred groups Z are OH, hydrogen, halogen, methoxy, ethoxy, —$NH_2$, ($C_{1-2}$ alkyl)amine, di($C_{1-2}$alkyl)amine, ($C_{1-2}$acetyl)amine, di($C_{1-2}$ acetyl)amine, mercapto, methylthio, ethylthio or —OP(O)(OH)$_2$. Typically, either all groups Z are OH, or one, two, three or four, preferably one or two groups Z are other than OH and the remainder are OH.

X is typically hydrogen or halogen, preferably hydrogen or fluorine.

Alternatively, where a carbon atom carries a group Z which is other than OH, then X on the same carbon atom may represent hydrogen, OH, halogen, $C_{1-6}$ alkoxy, —NR'R", —NR'COR", —N(COR')(COR"), —SR', —COOR', —OP(O)(OR')(OR"), or $C_{1-6}$ alkyl which is optionally substituted with one or two substituents selected from halogen, $NH_2$, OH and $C_{1-2}$ alkoxy, wherein R' and R" are identical or different and are selected from hydrogen and $C_{1-6}$ alkyl groups which are optionally substituted with one or two substituents selected from halogen, $NH_2$, OH and $C_{1-2}$ alkoxy. Particularly preferred groups X in this embodiment are OH, hydrogen, halogen, methoxy, ethoxy, —$NH_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio or —OP(O)(OH)$_2$.

Typically, either each X represents hydrogen, or one, two or three, preferably one, X is other than hydrogen and the remainder represent hydrogen.

Typically A is —O—, —SH—, —NH— or —N($C_{1-6}$) alkyl, preferably —O—, —SH—, —NH— or —N(Me)-. Typically, either all groups A are —O— or one, two or three, preferably one, A group is other than —O— and the remainder represent —O—.

n is typically 0, 1, 2 or 3, preferably 2.

As depicted in formula (I), (Ia) and (Ib), the bond Cl(R)-A in the terminal saccharide unit corresponding to the Glc unit of Le$^a$ or Le$^b$, may be unsaturated or saturated. Typically, this bond is saturated.

In a preferred embodiment, the imaging agent of the invention is a conjugate of an oligosaccharide with an imaging moiety, wherein the oligosaccharide is of formula (Ia) or (Ib) or salt or a PEGylated form thereof:

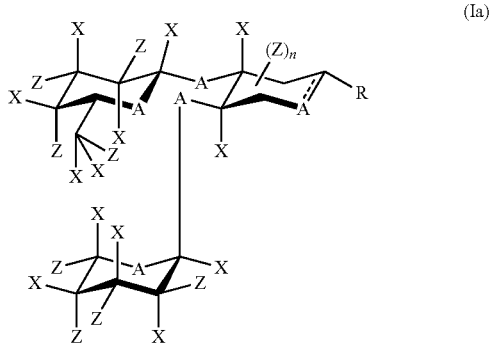

(Ia)

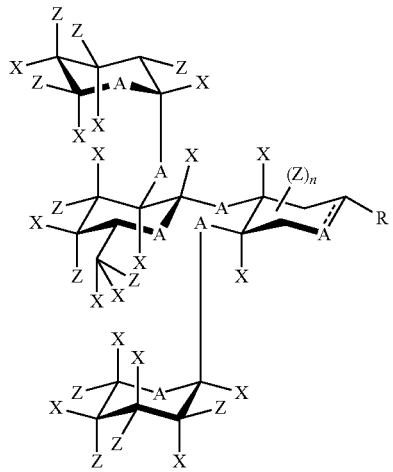

(Ib)

wherein:
each Z is the same or different and is selected from OH, hydrogen, halogen, methoxy, ethoxy, —$NH_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio and —OP(O)(OH)$_2$, wherein either all groups Z are OH, or one or two groups are other than OH and the remainder are OH;
each X is the same or different and is selected from hydrogen or halogen, or in the case where a group Z carried on the same carbon atom as X is other than OH, then X represents OH, hydrogen, halogen, methoxy, ethoxy, —$NH_2$, ($C_{1-2}$ alkyl)amine, di($C_{1-2}$alkyl)amine, ($C_{1-2}$acetyl)amine, di($C_{1-2}$ acetyl)amine, mercapto, methylthio, ethylthio or —OP(O)(OH)$_2$,
wherein either all groups X are hydrogen, or one or two groups are other than hydrogen and the remainder are hydrogen;
each A is the same or different and is selected from —O—, —SH—, —NH— and —N(Me)-; wherein either all groups A are —O— or one A group is other than —O— and the remainder represent —O—;
n is 2;
the bond Cl(R)-A is saturated; and
R represents the point of attachment to the imaging moiety.
In a further preferred embodiment,
each Z is the same or different and is selected from OH, hydrogen, halogen, methoxy, ethoxy, —$NH_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio and —OP(O)(OH)$_2$, wherein either all groups Z are OH, or one or two groups are other than OH and the remainder are OH;
each X is the same or different and is selected from hydrogen or halogen, wherein either all groups X are hydrogen, or one or two groups are halogen and the remainder are hydrogen;
each A is —O—;
n is 2;
the bond Cl(R)-A is saturated; and
R represents the point of attachment to the imaging moiety.

Most preferred oligosaccharides of formula (Ia) or (Ib) are Le$^a$ and Le$^b$, and their pharmaceutically acceptable salts, in particular Le$^a$ or a pharmaceutically acceptable salt thereof.

The Le$^a$ or Le$^b$ or mimetic thereof may be in the form of a salt. In particular, if a phosphate or sulphonate group is present, this may be in the form of a salt. For in vivo use, the salt will typically be a pharmaceutically acceptable salt. A pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutical acceptable bases include alkali metal (e.g. sodium or potassium) and alkaline earth metal (e.g. calcium or magnesium) hydroxides and organic bases such as alkyl amines, aralkyl amines or heterocyclic amines.

Tautomers of the conjugates of the invention defined above also form part of the invention. Also, conjugates defined above containing one or more chiral centre may be used in enantiomerically or diasteroisomerically pure form, or in the form of a mixture of isomers. The conjugates of the invention typically have more than one chiral centre, which gives rise to diastereoisomers, each of which consists of two enantiomers, with the appropriate (R)- or (S)-stereochemistry at each chiral centre. For the avoidance of doubt, the chemical structures depicted herein are intended to embrace all stereoisomers of the conjugates shown, including racemic and non-racemic mixtures and pure enantiomers and/or diastereoisomers.

For the avoidance of doubt, the conjugates of the invention can, if desired, be used in the form of solvates.

The oligosaccharide moiety may be PEGylated. Standard PEGylation techniques may be used, with the PEG group typically being bound to one of the OH groups on the saccharide. PEG groups of up to 500 units are typically used. Where the oligosaccharide is PEGylated, the PEG group is attached to the oligosaccharide at a position which does not carry the imaging moiety (i.e. the PEG group is not attached at R).

The oligosaccharide moiety is conjugated to an imaging moiety via the C1 carbon atom of the Glc saccharide unit (for example as depicted at R in formula (I)). The imaging moiety may be any imaging moiety which is envisaged for use in imaging of the endothelium. Imaging moieties useful in MRI, PET, SPECT and fluorescence-based systems are particularly envisaged.

Examples of imaging moieties useful in MRI include Gd(III)-containing contrast agents, iron containing colloidal particles and manganese containing particles.

Gd (III) containing contrast agents are, for example, complexes of Gd(III) with organic chelating agents. Examples of suitable chelating agents include tetraazocycloalkanes.

Suitable iron containing colloidal particles include those comprising iron hydroxide, iron oxide hydrate, iron (II) oxide, iron (III) oxide, mixed iron oxide, metallic iron or mixtures thereof. In mixed iron oxides other metal oxides such as oxides of cobalt, nickel, manganese, beryllium, magnesium, calcium, barium, strontium, copper, zinc, platinum, aluminium, chromium, bismuth, rare earth metals and mixtures thereof can be present. In preferred embodiments, the iron containing particle is an iron (II) or iron (III) oxide or an iron hydroxide or a mixture thereof. In a particularly preferred embodiment, the particle is iron oxide, in particular iron (III) oxide. The particles are preferably less than 1 mm in size, preferably less than 100 nm in size, and are typically less than 80 nm, preferably less than about 50 nm and may be as small as 5 nm.

The particles preferably are cross-linked iron oxide particles (CLIOs). Such particles are described for example in Wunderbaldinger et al, Acad Radiol 2002 9 (supple 2) S304-S306. These particles comprise a core of iron oxide, that is preferably 3 to 10 nm, preferably 3 to 5 nm in size, and a dextran coat. Preferably the dextran coat is formed by crosslinking the dextran to form a dextran chain around the iron oxide core. Typically such particles may be produced by reacting dextran coated iron oxide particles in presence of epichlorohydrin and ammonia. And our larger, biodegradable particles 300 nm-1 um cf our patent on mMPIO. Also we could hyperpolarise the sugars.

Examples of imaging moieties useful in PET include $^{18}$F, $^{11}$C and isotopes of oxygen.

Examples of imaging moieties useful in PET and SPECT include radiometals which are bound to organic chelating agents. Examples of radiometals which can be used are $^{64/67}$Cu, $^{90}$Y, $^{99m}$Tc, $^{186}$Re, $^{111}$In and $^{68}$Ga. $^{123}$I and a $^{131}$I can also be used. Examples of suitable organic chelating compounds are M-(CNtBu)$_4$(bpcg) (wherein M is a metal and bper is bipyridyl Congo Red), M-(CNtBu)$_4$(bper) (wherein M is a metal and bpcg is bipyridyl Chrisamine G), M-(CO)$_3$-3-OH, monoamide-monoaminedithiol (MAMA), bis-amine-bis-thiol (BTA), N,N'-bis[2-mercapto-2-methylpropyl]2-aminobenzylamine (UBTA), diethylene triamine pentaacetic acid (DTPA), 1,4,7-triazacyclononane-N,N',N"-triacetic acid (NOTA), 3,6,9,15-tetraaza bicyclo[9.3.1]-pentadeca-1(15),11,13-triene-3,6,9-triacetic acid (PCTA), cyclen and cyclen derivatives and 1,4,7,10-tetraazacyclododecane-1,4,7,10-tetraacetic acid (DOTA).

Imaging agents useful in fluorescence-based imaging techniques may also be used, such as quantum dots (CdS or derivatives), as well as particles, capsides, dendrimers or polymers labelled with a fluorescent moiety detectable between 350 nm and 1100 nm.

Iron containing colloidal particles are preferred for use as the imaging moiety.

Imaging moieties such as those described above can be derivatised with a functional group, for example with amine containing groups, for conjugation to the oligosaccharide moieties described herein. The manner in which this conjugation is achieved is not particularly limited and the skilled chemist would be able to devise suitable synthetic strategies and functional groups to use. For example, amino groups of a dextran-coated iron oxide particle can react with a 2-cyanomethyl-containing oligosaccharide to produce an imaging agent of the invention. Alternative functional groups which can be used include 2-imino-2-methoxyethyl, isothiocyanide, carboxylic acid, activated ester, sulfonyl halide, aldehyde, ketone, tosyl and epoxide, each of which can be used to react with an amine group on an imaging agent. Similarly, maleimide, iodoacetamide and thiol functional groups may be used to react with thiol groups on an imaging agent. Click chemistry can alternatively be used between azide and alkyne moieties or derivatives. Protein site specific recognition and especially the streptavidin/biotin system can be used. Further, whilst it is mentioned above that the nucleophilic moieties are introduced on the oligosaccharides and the electrophilic moieties on the imaging moiety, the reverse is also possible.

Typically, the imaging moieties, derivatised if necessary as described above, are directly bound to the oligosaccharide moiety. However, if desired, linking groups may be present between the oligosaccharide moiety and the imaging moiety. For example, $C_{1-6}$ alkyl groups, which may contain or terminate in an —O—, —S—, —NR— or arylgroup, where R is hydrogen or $C_{1-6}$alkyl, can be envisaged as suitable linking groups between the two moieties.

$Le^a$ and $Le^b$ can be prepared as set out in Schemes 1a and b and 2a and b below:

Synthesis of Lewis a
Scheme 1a
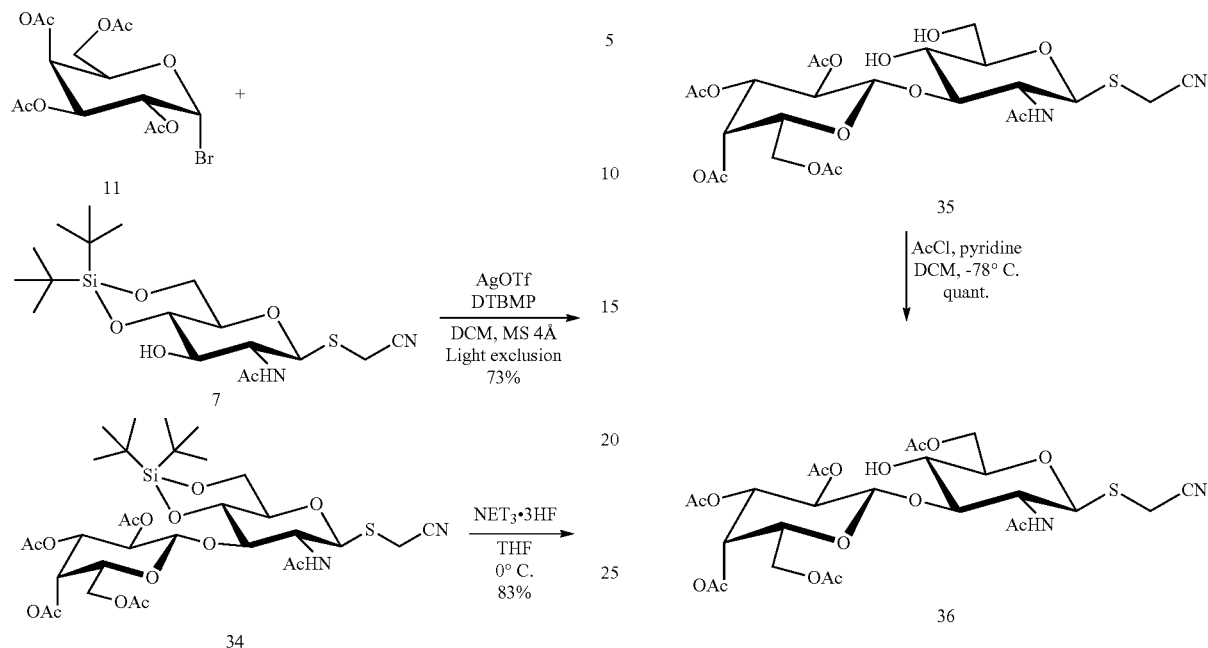
Scheme 1b
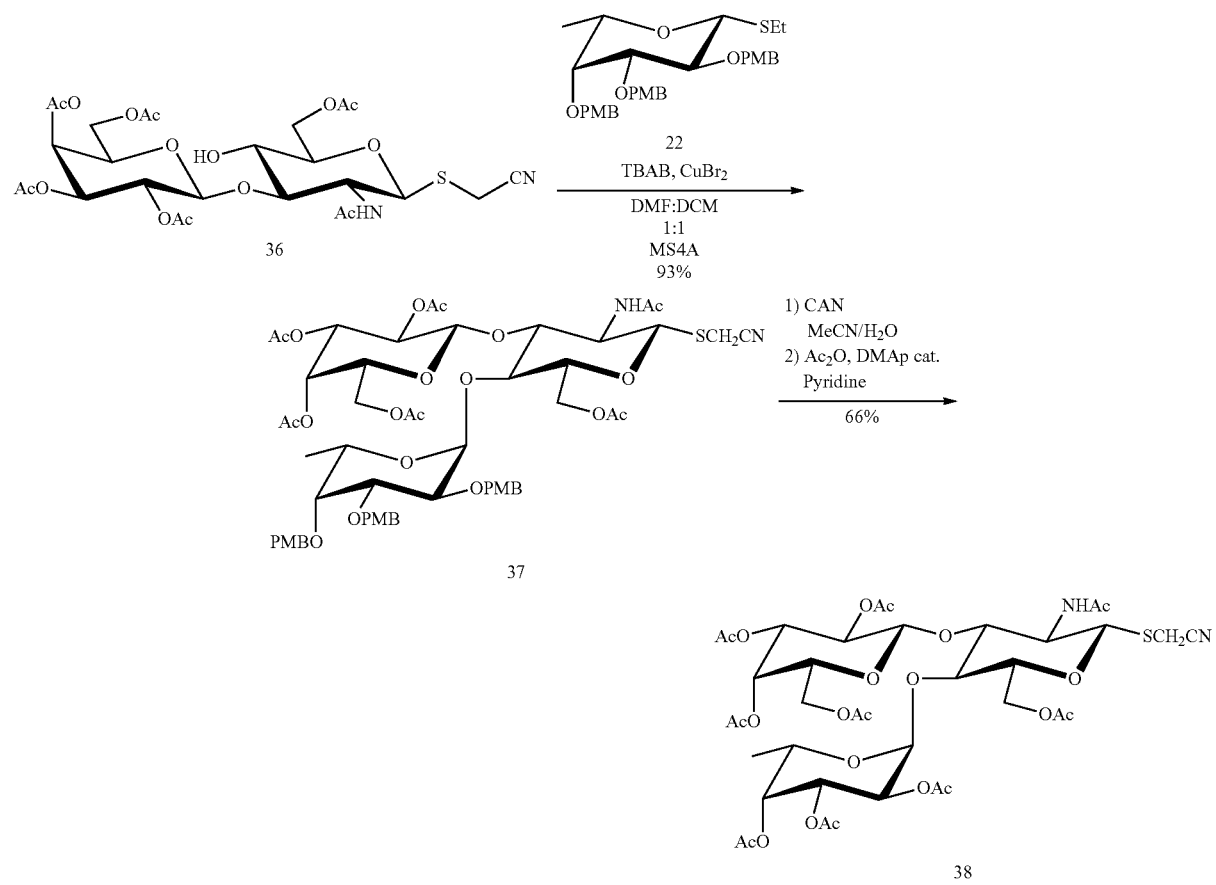

Synthesis of Lewis b
Scheme 2a
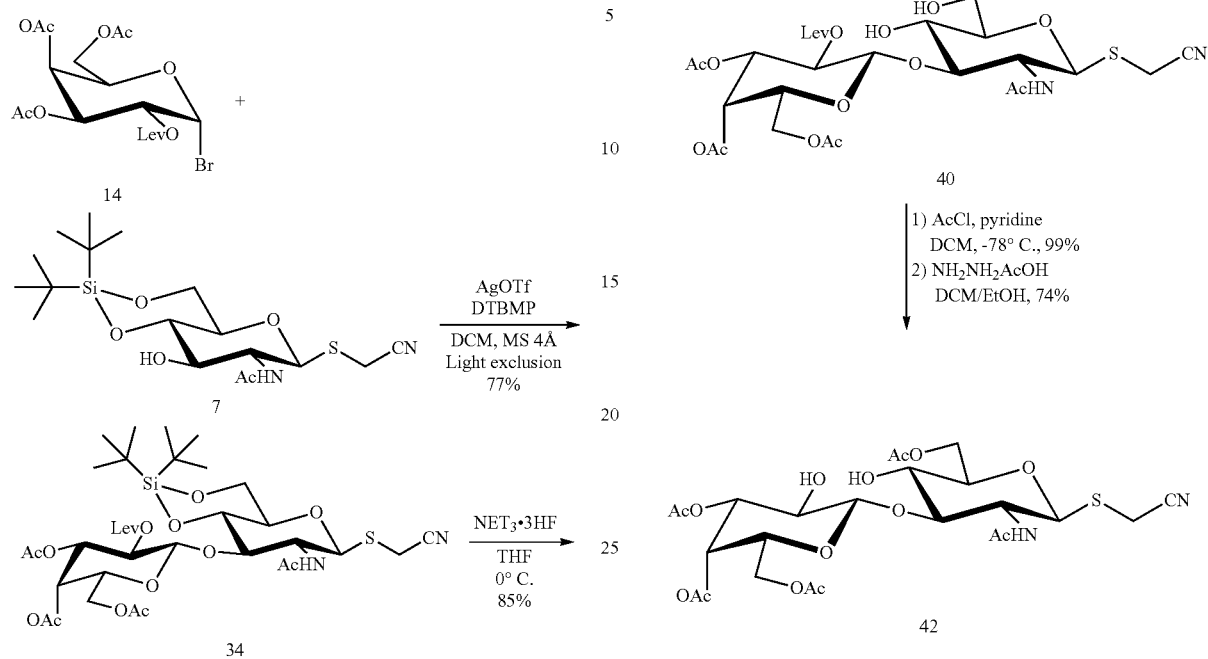
Scheme 2b
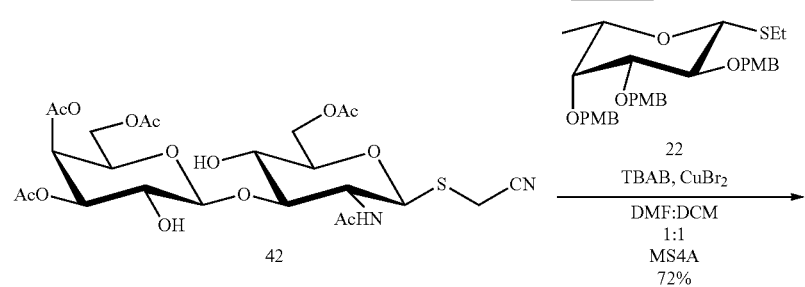
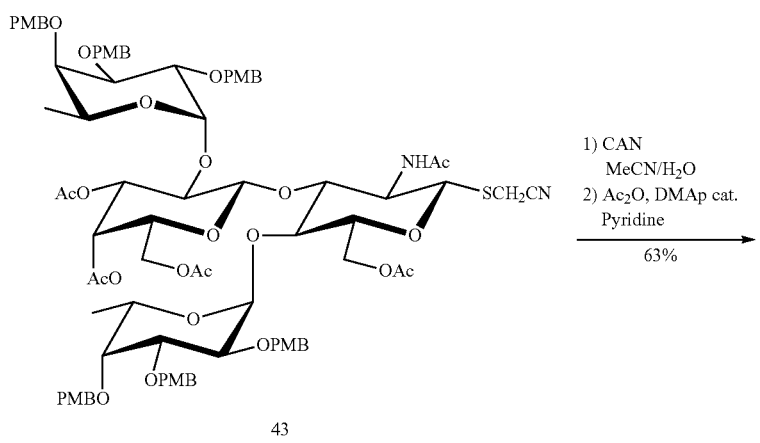

-continued

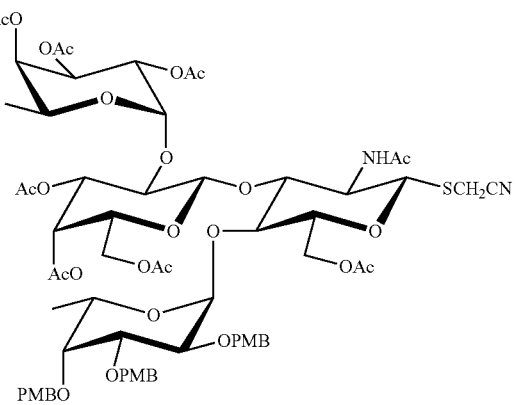

43

Schemes 1 and 2 above provide the oligosaccharide with a reactive —SCH$_2$CN group at the position which is to conjugate with the imaging moiety. Thus, an imaging moiety derivatised with an amine group can be reacted with the Lewis A and Lewis B sugars thus produced to provide a conjugate according to the invention. The AcO groups can be removed by standard deprotection techniques. Further detail regarding the synthetic route to Lewis A and Lewis B is provided in the Examples.

The mimetics of Le$^a$ and Le$^b$ can be prepared by adaptation of the above Schemes in an appropriate way, as would be familiar to the skilled chemist. For instance, the GluNAc moiety could be replaced by a cyclohexyl ring substituted by different substituents to graft the Gal and Fuc moieties. Cyclohexanediol can be used to synthesize this type of mimetic. The O-glycosidic linkages could be switch to C-, S- or amide glycosidic linkages. The hydroxyl groups could be also modified by different substituents using previously modified monosaccharide units.

The conjugates of the invention can be formulated for use by combining in a pharmaceutical composition with a pharmaceutically acceptable carrier or diluent. The compositions are typically prepared following conventional methods and are administered in a pharmaceutically suitable form.

Solid oral forms of the composition of the invention may contain, together with the conjugated particles themselves, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such compositions may be manufactured in known manner, for example, by means of mixing, granulating, tabletting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the conjugated particles of the invention, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions. Most preferably the composition comprises a conjugate according to the invention and saline.

The conjugates according to the present invention can be used as contrast agents in methods of medical imaging. The conjugates of the present invention are particularly useful as contrast agents using magnetic resonance imaging (MRI), Positron Emission Tomography (PET), Single-Photon-Emission-Computed Tomography (SPECT) and fluorescence-based imaging techniques, in particular MRI, for example in combination with an imaging moiety formed of an iron containing colloidal particle.

Imaging may be carried out on a subject to whom the imaging agent of the invention has been pre-administered. Such a subject will typically have the imaging agent of the invention present in the blood stream.

The imaging method of the invention in one aspect comprises a step of administering the imaging agent to the patient, followed by carrying out medical imaging. The imaging agents can be delivered to the patient under investigation by any suitable route, but are typically provided by injection, usually intravenous injection.

The imaging agents of the invention can be used to image the endothelium through the ability of the oligosaccharide groups to bind to endothelial cells in vivo. The present invention is therefore useful in imaging of endothelial cells. Further, Lewis A and its mimetics and derivatives bind to neutrophils, whilst Lewis B and its mimetics and derivatives bind to monocytes. Thus, the particular oligosaccharide group used in the imaging agent can be selected so as to provide the desired imaging pattern. In particular, when the oligosaccharide is Lewis A or a mimetic or derivative thereof, imaging of neutrophils can be carried out. Further, when the oligosaccharide is Lewis B or a mimetic or derivative thereof, imaging of monocytes can be carried out.

The imaging agents of the present invention may also be used in the monitoring or diagnosis of disease. The agents of the invention may cross the blood brain barrier and so may be particularly useful in the monitoring or diagnosis of conditions affecting the brain. In a preferred embodiment, the conjugates are used in the monitoring and diagnosis of inflammation. The conjugates may also be useful for the monitoring and diagnosis of tumours, as well as non-symptomatic inflammatory diseases and autoimmune diseases.

In a particularly preferred embodiment according to the present invention, the imaging agents of the invention are used in the monitoring and diagnosis of inflammation in the brain, and are particularly useful in the diagnosis of multiple sclerosis and other diseases with an inflammatory (activation of the endothelium) component including vascular dementia, neuromyelitis optica, stroke, diffuse head injury, Alzheimer disease. The conjugates of the present invention have the advantage of crossing the blood brain barrier and so may be used to provide an indication of inflammation and other disorders in the brain before the condition is advanced.

The dosages in which the compositions according to the invention are administered will vary according to the mode of use and the route of use, as well as to the requirements of the subject. Typically, the imaging agents of the invention will be administered in an amount which provides an equivalent dosage of the imaging moiety as is typically used for the imaging moiety in question when not bound to an oligosaccharide in accordance with the invention.

The present invention further relates to the therapeutic treatment of diseases by compounds which are selected from the oligosaccharides Le$^a$, Le$^b$ and their mimetics, as well as pharmaceutically acceptable salts and PEGylated forms of these oligosaccharides. In this aspect of the invention, the oligosaccharides are of formula (III):

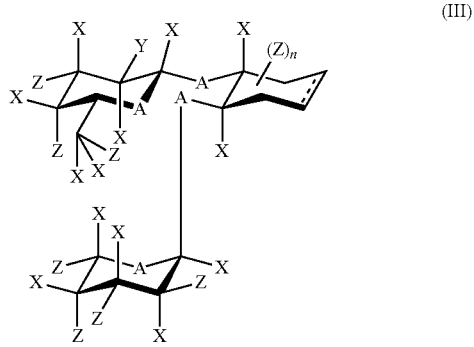

(III)

wherein Z, X, Y, A and n are as defined herein. In the oligosaccharides of formula (III), A is typically —O— or —SH—. Typically, either all groups A are —O— or one, two or three, preferably one, A group is —S— and the remainder represent —O—.

Most preferred compounds for therapeutic treatment are Le$^a$ and Le$^b$, and their pharmaceutically acceptable salts, in particular Le$^a$ or a pharmaceutically acceptable salt thereof.

The compounds for therapeutic treatment may be in the form of a salt. In particular, if a phosphate or sulphonate group is present, this may be in the form of a salt. For in vivo use, the salt will typically be a pharmaceutically acceptable salt. Suitable pharmaceutically acceptable salts are described above.

Tautomers of the oligosaccharides of formula (III) defined above also form part of the invention. Also, oligosaccharides of formula (III) defined above containing one or more chiral centre may be used in enantiomerically or diastereoisomerically pure form, or in the form of a mixture of isomers. For the avoidance of doubt, formula (III) depicted herein is intended to embrace all stereoisomers of the oligosaccharides shown, including racemic and non-racemic mixtures and pure enantiomers and/or diastereoisomers.

For the avoidance of doubt, the oligosaccharides of formula (III) can, if desired, be used in the form of solvates.

The compounds for therapeutic treatment may be PEGylated. Standard PEGylation techniques may be used, with the PEG group typically being bound to one of the OH groups on the saccharide. PEG groups of up to 500 units may be used.

The oligosaccharides of formula (III) may be prepared as described above with reference to the Lewis A and Lewis B sugars, but replacing starting material 7 with the alternative starting material 7a:

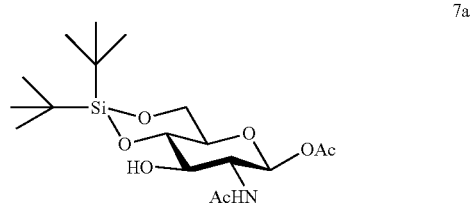

7a and subsequently carrying out appropriate deprotection of the OAc group at the C1 position.

The compounds for therapeutic treatment are typically formulated as a composition together with a pharmaceutically acceptable carrier or diluent. Suitable compositions, and carriers and diluents, are as described above with regard to the imaging agents of the invention. The compositions may be administered in a dosage which is selected according to the nature and severity of the disease or condition to be treated and factors connected with the patient, in particular the age and body weight, as well as other relevant factors. The dosage given is typically in the range of from 1 mg to 3 g per day.

The compounds for therapeutic treatment and their compositions may be useful in the treatment of diseases and disorders wherein binding of circulating cells to the endothelium occurs. In particular, these compounds and compositions may be useful in the treatment of inflammatory diseases, autoimmune diseases and cancer. Particular diseases and conditions which the compounds and compositions may be use to treat include osteoarthritis, burns, spinal cord injury, stroke, ischeamic heart disease, atherosclerosis, multiple sclerosis, rheumatoid arthritis, inflammatory bowel disease, graft versus host disease and metastasis.

The invention will now be described with reference to the following Examples. Reference numerals in Examples 1 and 2 refer to Schemes 1a, 1b, 2a and 2b above.

EXAMPLES

Example 1: Synthesis of Lewis A

Step 1a: 2-N-Acetamido-3,4,6-tri-O-acetyl-2-deoxy-1-chloro-β-D-glucopyranoside 2

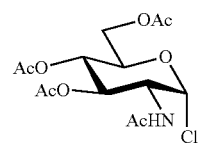

Acetyl chloride (58.1 mL, 831.6 mmol, 9 eq.) was placed in a 250 mL round-bottom flask and N-Acetyl glucosamine 1 (20.0 g, 90.4 mmol, 1.0 eq.) was added within 3 min under strong stirring and Ar-atmosphere. The suspension is stirred for 2 days at 25° C. before CHCl₃ (200 mL) was added to the slightly discoloured solution. The mixture is poured under strong stirring onto ice (200 g) and H₂O (50 mL). Phases were separated and the organic layer transferred without delay into a 1 L beaker with ice (100 g) and satd. NaHCO₃-solution (250 mL). The mixture was shortly stirred, transferred to a separatory funnel and shaken until the gas-production ended. Phases were separated, MgSO₄ (15 g) was added to the organic layer, stirred for no longer than 10 min, filtrated and the solvents concentrated under vacuum to a volume of about 20 mL before Et₂O (250 mL) was rapidly added and the solution allowed to crystallize at 25° C. Formed crystals are filtered off (22.5103 g) and the mother liquor evaporated to give a syrup, which on addition of 30 mL Et₂O yielded more of the chloride (1.3437 g) to yield 2 as colourless crystals (23.854 g, 65.22 mmol, 72%). TLC: $R_f$=0.47 (EtOAc neat).

Step 1b: S-thiouronium 2-N-Acetamido-3,4,6-tri-O-acetyl-2-deoxy-1-thio-β-D-glucopyranoside 3

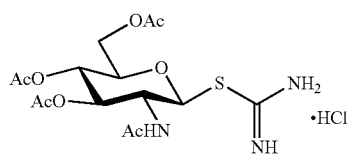

Crude chloride 2 (23.854 g, 65.22 mmol, 1.0 eq.) was dissolved in dry acetone (200 mL). Thiourea (9.93 g, 130.44 mmol, 2 eq.) was added, and the mixture heated to reflux (80° C.). After 2 h the solution is cooled to 25° C., filtrated and the solids washed with ice-cold dry EtOH (30 ml). The filtrate is concentrated to dryness, dissolved in acetone under heat and allowed to crystallize at 25° C. Filtration, washing, and drying of the combined solid fractions gave 3 as white powder (23.3931 g, 52.94 mmol, 81%). TLC: $R_f$=0.2 (MeOH neat).

Step 1c: S-cyanomethyl 2-N-Acetamido-3,4,6-tri-O-acetyl-2-deoxy-1-thio-β-D-glucopyranoside 4

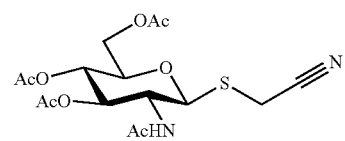

S-thiouronium 2-N-Acetamido-3,4,6-tri-O-acetyl-2-deoxy-1-thio-β-D-glucopyranoside 3 (23.3 g, 52.7 mmol, 1.0 eq.) was dissolved in a water/acetone mixture (1:1, 240 mL) and sodium metabisulphite (22.0 g, 115.9 mmol, 2.2 eq.), potassium carbonate (9.5 g, 68.5 mmol, 1.3 eq.) and chloroacetonitrile (63.4 mL, 1.0 mol, 19 eq.) were added. After 16 h at 25° C. the solution was poured on ice-water (500 mL) and stirred for another 1 h. The mixture was transferred to a separatory funnel and the organic material extracted with CH₂Cl₂ (3×250 mL). The combined organic layers were washed with ice-cold brine (2×250 mL), filtered through cotton, solvents evaporated, and twice codestilled with acetone. The title compound 4 was obtained as white powder (24.6 g, 61.0 mmol, quant.) which was used without further purification in the next reaction. TLC: $R_f$=0.60 (EtOAc: MeOH, 8:2).

Steph 1d: S-cyanomethyl 2-N-Acetamido-2-deoxy-1-thio-β-D-glucopyranoside 5

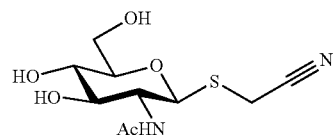

To a suspension of tetraacetate 4 (17.3 g, 43.0 mmol, 1.0 eq.) in MeOH (340 mL), Et₃N (34.0 mL, 240.7 mmol, 5.6 eq.) was added and stirred at r.t. for 24 h. Solvents were removed under high vacuum and the crude mixture was coevaporated with toluene (2×20 mL) to afford 5 as a white powder (12.7 g, 45.9 mmol, quant.) which was used for the next step without further purifications. TLC: $R_f$=0.14 (EtOAc:MeOH, 8:2).

Step 1e: S-cyanomethyl 2-N-Acetamido-4,6-O-di-tert-butylsilylidene-2-deoxy-1-thio-β-D-glucopyranoside 7

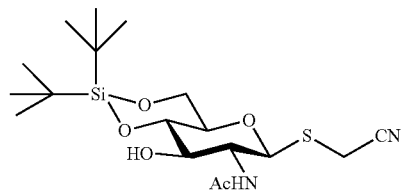

To 5 (5.0 g, 17.9 mmol, 1 eq) in anhydrous degaz DMF (80 mL) at −40° C. (Dry ice/MeCN) was slowly added di-tert-butylsilyl bis(trifluomethanesulfonate) (6.2 mL, 18.8 mmol, 1.05 eq). The mixture was stirred overnight from −40° C. to 0° C. under N2. Pyridine (5 mL) was then added and stirred for 10 min at 4° C. to quench the reaction before evaporation under vacuum. The crude was co-evaporated 3 times with toluene before purification by flash chromatography over silica (biotage gradient DCM 0% to 5% MeOH in DCM follow by an isocratic gradient of 15% MeOH in DCM) to afford 7 as a white anamorphous powder (5.7 g, 21.1 mmol, 76%).

Step 1f: 1-bromo-2,3,4,6-tetra-O-acetyl-D-galactopyranose 11

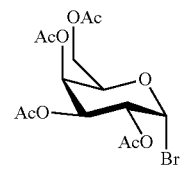

1,2,3,4,6-penta-O-acetyl-β-D-galactopyranose (20.00 g, 57.47 mmol) was dissolved in CH$_2$Cl$_2$ (123 mL) and HBr in HOAc (33% v/v, 28 mL). The mixture was stirred for 2 h at room temperature. Then the organic phase was washed with saturated aqueous NaHCO$_3$ (1×100 mL, 2×50 mL) and brine (1×10 mL). After drying (MgSO$_4$) and concentration, 1-bromo-2,3,4,6-tetra-O-acetyl-D-galactopyranose 11 (16.75 g, 40.73 mmol, 71%) was obtained as a white amorphous powder (stored at −20° C.) and was used for the next step without further purification.

Step 1g: S-ethyl 2,3,4-tri-O-p-methoxybenzyl-6-deoxy-1-thio-β-L-galactopyranoside 22

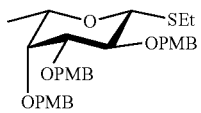

To a solution of L-Fucose (25.0 g, 152.3 mmol, 1.0 eq) in dry pyridine (200.0 mL) was added acetic anhydride (130 mL, 1307.7 mmol, 9.0 eq). The reaction was stirred at rt ON. Solvent were evaporated under high vacuum and the crude mixture was co-evaporated 3 times with toluene to afford 18 (TLC: R$_f$=0.50, EtOAc:PE, 8:2) which was directly diluted in DCM (600 mL) under argon. Hydrogen bromide 33% in acetic acid (330 mL, 1828.0 mmol, 12 eq) was added ad the reaction was stirred at rt for 2 h. The crude mixture was poured into a mixture of water and ice (1 L) and extract with DCM (2×500 mL). The combined organic layers were washed with water (500 mL), NaHCO$_3$ sat. (500 mL) and brine (500 mL), dried over MgSO$_4$, filtered and concentrated in vacuo. The crude 19 was then dissolved in acetone (440 mL) and EtOAc (22 mL). Ethyl mercaptan (13 mL, 175.1 mmol, 1.15 eq) was then added follow by KOH (96.2 g, 175.1 mmol, 1.15 eq) in EtOH (92.2 mL). The solution was stirred at rt for 16 h and diluted in 500 mL DCM. The solution was washed with NaHCO$_3$ sat. (600 mL) and brine (600 mL), dried over MgSO$_4$, filtered and concentrated under vacuo to afford the crude 20, which was used as it for the next step.

To the crude 20 dissolved in dry MeOH (150 mL) was added sodium methoxide (9.5 g, 175.1 mmol, 1.15 eq). The solution was stirred at rt for 1 h before neutralization with Dowex H+ form and filtered. The crude mixture and tetrabutylammonium iodide (5.6 g, 15.23 mmol, 0.1 eq) in dry DMF (610 mL) were cooled at 0° C. before sodium hydride 60% in oil suspension (37 g, 913.8 mmoL, 6.0 eq) was added. The solution was stirred at 0° C. 30 min and paramethoxybenzyl chloride (83 mL, 609.2 mmol, 4 eq) was added. The solution was allowed to warm to r.t. and stirred 22 h. Methanol was added at 0° C. to quenched the reaction and the solution was concentrated in vacuo, diluated in EtOAc (500 mL) and washed with Brine (4×400 mL), dried over MgSO4, filtered and re-concentrated in vacuo before purification by flash chromatography over silica (PE:EtOAc, 9:1, 85:15, 8:2) which provide 22 as slightly yellow powder (43 g, 75.6 mmol, 50%). TLC: R$_f$=0.66 (EtOAc neat).

Step 1h: S-cyanomethyl 2-N-acetimido-4,6-O-di-tert-butylsilylidene-3-O-[2,3,4,6-tetra-O-acetyl-β-D-galactopyranosyl]-2-deoxy-1-thio-β-D-glucopyranoside 34

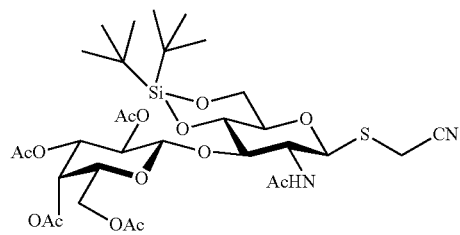

Acceptor 7 (1.0 g, 2.4 mmol, 1 eq) and donor 11 (1.5 g, 3.6 mmol, 1.5 eq) were co-evaporated twice with toluene and dry under high vacuum for 1 h. DCM (24 mL) and MS4 Å (2.4 g) were then added and the solution was stirred at r.t. for 1 h before addition of DTBMP (493 mg, 2.4 mmol, 1 eq) and AgOTf (1.4 g, 5.5 mmol, 2.3 eq). The mixture was covered by aluminium foil and stirred at r.t. After 2.5 h the reaction mixture was filter over Celite and rinse with DCM. After removal of the solvent, the residue was purified by flash chromatography on silica (biotage gradient 12% to 100% EtOAc in PE) to afford 34 as a white anamorphous solid (1.3 g, 1.7 mmol, 71%).

Step 1i: S-cyanomethyl 2-N-acetimido-3-O-[2,3,4,6-tetra-O-acetyl-β-D-galactopyranosyl]-2-deoxy-1-thio-β-D-glucopyranoside 35

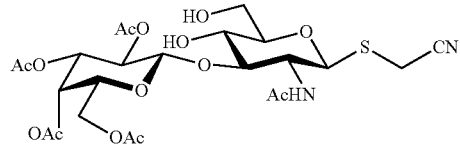

To protected 34 (1.2 g, 1.6 mmol, 1 eq) in dry THF (16 mL) at 0° C. was added NEt$_3$.3HF (530 µt, 3.3 mmol, 2.1 eq). After 3 h solvent were evaporated. The crude residue was purified by flash chromatography over silica (biotage gradient, 0% to 5% MeOH in EtOAc) to afford 35 as a white anamorphous solid (777.3 mg, 1.3 mmol, 87%).

Step 1j: S-cyanomethyl 2-N-acetimido-6-O-Acetyl-3-O-[2,3,4,6-tetra-O-acetyl-β-D-galactopyranosyl]-2-deoxy-1-thio-β-D-glucopyranoside 36

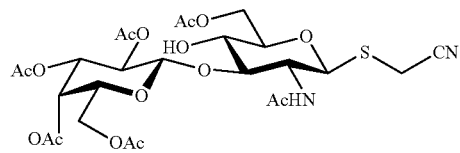

To unprotected disaccharide 35 (735.0 mg, 1.2 mmol, 1 eq) in dry DCM (17 mL) and dry pyridine (360 µL, 4.4 mmol, 4 eq) under argon at −78° C. was added AcCl (200 µL, 2.7 mmol, 2.5 eq). After 1 h methanol was added to quench the reaction and stirred a bit at −78° C. The crude was dissolve in DCM (200 mL) and washed with HCl 1N (100 mL), NaHCO₃ (100 mL), Brine (100 mL) and dried over MgSO₄. Evaporation of the solvent to dryness afford 36 as a white anamorphous solid (801.0 mg, 1.2 mmol, quant.)

Step 1k: S-cyanomethyl 2-N-acetamido-6-O-acetyl-4-O-[2,3,4-tri-O-p-methoxybenzyl-6-deoxy-α-L-galactopyranosyl]-3-O-[2,3,4,6-tetra-O-acetyl-β-D-galactopyranosyl]-2-deoxy-1-thio-β-D-glucopyranoside 37

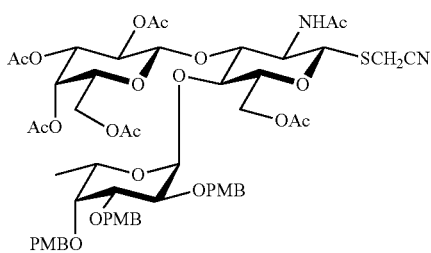

36 (1.4 g, 2.2 mmol, 1.0 eq) and 22 (2.5 g, 4.4 mmol, 2.0 eq) (co-evaporated 3× with toluene and dried under high vacuum for 1 h) were dissolved in dry DCM:DMF 1:1 mixture (4.4 mL) and MS4 Å (2.2 g) and stirred 1 h at rt before copper(II) bromide (987.0 mg, 4.4 mmol, 2.0 eq) and tetra-butylammonium bromide (1.5 g, 4.6 mmol, 2.1 eq) were added.

The mixture was stirred at rt overnigth with light exclusion. The crude mixture was filtered over celite and washed with EtOAc (400 mL). The filtrate was washed with NH₄Cl sat pH 8.5 aqueous solution (3×200 mL) and brine (200 mL). The organic layers was dried over MgSO₄, filtered, concentrated in vacuum and purified by flash chromatography (biotage gradient, 50% to 100% EtOAc in PE) to afford 37 as a white cream foam (2.3 g, 2.0 mol, 91%).

Step 1l: S-cyanomethyl 2-N-acetamido-6-O-acetyl-4-O-[2,3,4-tri-O-acetyl-6-deoxy-β-L-galactopyranosyl]-3-O-[2,3,4,6-tetra-O-acetyl-β-D-galactopyranosyl]-2-deoxy-1-thio-β-D-glucopyranoside 38

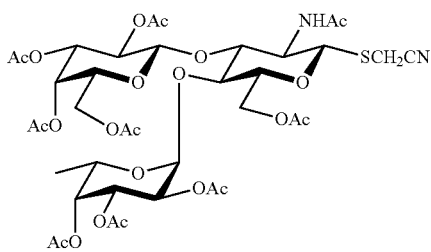

To 37 (2.2 g, 1.9 mmol, 1.0 eq) dissolved in a mixture of MeCN:H₂O (9:1, 39.0 mL) was added CAN (6.9 g, 12.6 mmol, 6.5 eq). The solution was stirred at r.t. for 7 h before acetic anhydride (165 mL), Pyridine (165 mL) and DMAP (24 mg, 0.2 mmol, 0.1 eq) were added. The mixture was stirred ON at r.t. before MeOH was added to quench the reaction. Solvent (with co-distillation with toluene 3 times) and the crude mixture was diluted in EtOAc (500 mL). The organic layer was washed with HCl 1M (3×200 mL), NaHCO₃ sat. aqueous solution (3×200 mL), Brine (200 mL, dried over MgSO₄, filtered and concentrated under vacuo. The crude mixture was then purified by flash chromatography over silica (biotage, 70% to 100% EtOAc in PE) follow by a water wash afford 38 a white anamorphous solid (1.2 g, 1.3 mmol, 68%).

Step 1m: S-cyanomethyl 2-N-acetamido-4-O-[6-deoxy-α-L-galactopyranosyl]-3-O-[β-D-galactopyranosyl]-2-deoxy-1-thio-β-D-glucopyranoside 23

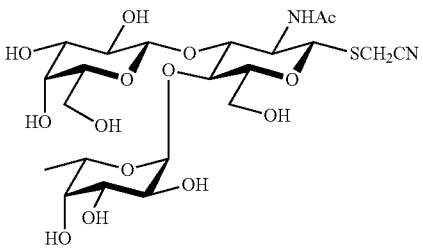

Acylated modified Le$^a$ 38 (10.0 mg, 10.9 μmol) was disolved in MeOH (109 μL). MeONa (25% solution, 2.483 μL) was added and the mixture was stirred for 5 min at room temperature. The reaction was quenched by introduction of ion exchange resin (Dowex, 100-200 mesh). After filtration and concentration (N₂ flow), the modified Le$^a$ 23 (8.4 mg, 9.2 μmmol, 84%) was isolated as an amorphous white powder. $^1$H NMR (500 MHz, MeOD) δ 5.05 (d, J=3.9 Hz, 1H, H"-1), 4.88 (dq, J=6.7, 0.6 Hz, 1H, H"-5), 4.72 (br d, J=9.9 Hz, 1H, H-1), 4.44 (d, J=7.6 Hz, 1H, H'-1), 4.06 (m, 1H, H-2), 4.01 (m, 1H, H-3), 3.96 (dd, J=12.4, 2.3 Hz, 1H, H-6a), 3.92 (dd, J=12.4, 3.5 Hz, 1H, H-6b), 3.86 (dd, J=10.2, 3.3 Hz, 1H, H"-3), 3.85 (d, J=17.1 Hz, 1H, SCHCN), 3.84-3.80 (m, 1H, H-4), 3.76 (dd, J=10.9, 4.0 Hz, 1H, H'-6a), 3.76 (dd, J=10.2, 4.0 Hz, 1H, H"-2), 3.74 (dd, J=3.4, 0.6 Hz, 1H, H"-4), 3.74 (dd, J=3.3, 0.8 Hz, 1H, H'-4), 3.69 (dd, J=11.4, 4.9 Hz, 1H, H'-6b), 3.63 (d, J=17.0 Hz, 1H, SCHCN), 3.52 (dd, J=9.5, 7.6 Hz, 1H, H'-2), 3.47 (ddd, J=9.7, 3.5, 2.4 Hz, 1H, H-5), 3.43 (ddd, J=6.9, 4.9, 0.8 Hz, 1H, H'-5), 3.42 (dd, J=9.6, 3.3 Hz, 1H, H'-3), 1.99 (s, 3H, NHAc), 1.20 (d, J=6.6 Hz, 3H, H"-6). $^{13}$C NMR (126 MHz, MeOD) δ 174.0 (NHC(=O)CH₃), 118.5 (CN), 105.1 (C'-1), 99.7 (C"-1), 84.7 (C-1), 82.1 (C-5), 79.6 (C-3), 76.8 (C'-5), 74.8 (C'-3), 73.7 (C"-4), 73.4 (C-4), 72.2 (C'-2), 71.2 (C"-3), 70.0 (C"-2), 69.8 (C'-4), 67.7 (C"-5), 62.9 (C'-6), 61.4 (C-6), 55.8 (C-2), 23.0 (NHC(=O)CH₃), 16.6 (H"-6), 14.9 (SCH₂CN). HRMS (m/z): calcd for C₂₂H₃₆N₂NaO₁₄S, 607.1779 ([M+Na]$^+$). Found 607.1781.

Step 1n: Mixture of S-cyanomethyl 2-N-acetamido-4-O-[6-deoxy-α-L-galactopyranosyl]-3-O-[β-D-galactopyranosyl]-2-deoxy-1-thio-β-D-glucopyranoside 23 and S-2-imino-2-methoxyethyl 2-N-acetamido-4-O-[6-deoxy-α-L-galactopyranosyl]-3-O-[β-D-galactopyranosyl]-2-deoxy-1-thio-β-D-glucopyranoside 45

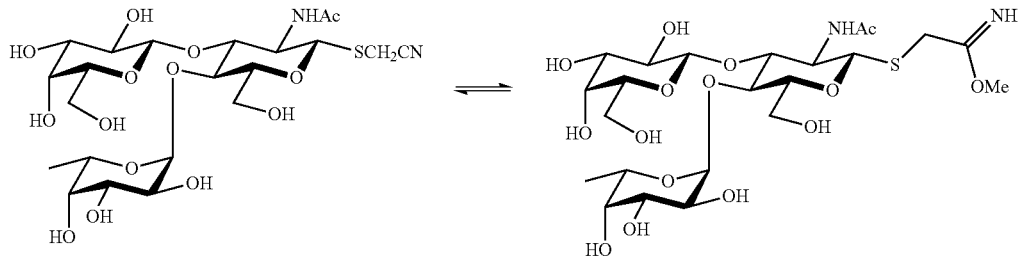

Acylated modified Le$^a$ 38 (51.4 mg, 55.9 μmol) was dissolved in anhydrous MeOH (598.3 μL) under argon. NaOMe (1M, 22.34 μL, 0.4 equiv) was added and the mixture was stirred for 24 h at room temperature. After concentration (N$_2$ flow for 30 min and high vacuum for 1 h), a mixture of the activated oligosaccharide 4-O-[6-deoxy-α-L-galactopyranosyl]-3-O-[β-D-galactopyranosyl]-1-(1-thio-S-2-imino-2-methoxyethyl)-2-acetamido-2-deoxy-β-D-glucopyranoside 45 and of the non-activated oligosaccharide 4-O-[6-deoxy-α-L-galactopyranosyl]-3-O-[β-D-galactopyranosyl]-1-thio-S-cyanomethyl-2-acetamido-2-deoxy-β-D-glucopyranoside 23 was obtained (36.0 mg, 51.7 mol % and 53.0 mass % of 45).

Example 2: Synthesis of Lewis B

Step 2a: 1,3,4,6-tetra-O-acetyl-a-D-galactopyranose 12

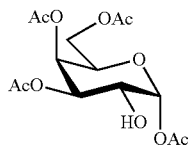

1,2,3,4,6-penta-O-acetyl-β-D-galactopyranose (50.03 g, 128.2 mmol) was dissolved in TFA/H$_2$O 10:1 (193 mL). The mixture was stirred for 5 h at room temperature. Then the EtOAc was evaporated and the residue was co-evaporated with toluene (3*30 mL) before dilution in diisopropylether (500 mL) to concretize a precipitate. After 45 min stirring at rt, 1,3,4,6-tetra-O-acetyl-α-D-galactopyranose 12 (21.16 g, 60.74 mmol, 47%) was isolated as a white amorphous solid by filtration and wash (3*150 mL diisopropylether). The compound was used for the next step without further purification.

Step 2b: 1,3,4,6-tetra-O-acetyl-2-O-levulinoyl-α-D-galactopyranose 13

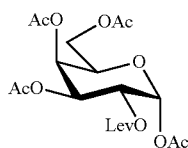

1,3,4,6-tetra-O-acetyl-D-galactopyranose 12 (17.00 g, 48.81 mmol) and levunilic acid (6.91 g, 6.94 mmol, 1.2 equiv) were dissolved in anhydrous DCM (195 mL). N-(3-Dimethylaminopropyl)-N'-ethylcarbodiimide hydrochloride (18.76 g, 95.90 mmol, 2.0 equiv), triethylamine (6.81 mL, 48.8 mmol, 1.0 equiv) and dimethylaminopyridine (1.19 g, 9.76 mmol, 0.2 equiv) were introduced and the mixture was stirred at room temperature for 5 h. The mixture was washed with water (1×250 mL), HCl 1N (2×250 mL), NaHCO$_3$ (1×300 mL) and brine before drying over MgSO$_4$ and concentration. 1,3,4,6-tetra-O-acetyl-2-O-levulinoyl-□-D-galactopyranose 13 (20.27 g, 45.41 mmol, 93%) was isolated as a translucent oil and was used for the next step without further purification.

Step 2c: 3,4,6-tri-O-acetyl-2-O-levulinoyl-1-bromo-α-D-galactopyranose 14

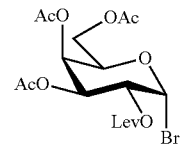

1,3,4,6-tetra-O-acetyl-2-O-levulinoyl-β-D-galactopyranose 13 (19.0 g, 42.5 mmol) was dissolved in hydrobromic acid 33% wt. in acetic acid solution (42.0 mL, 1.0 mL/mmol, 240.0 mmol, 5.6 equiv) and acetic anhydride (6.0 mL, 0.14 mL/mmol, 63.5 mmol, 1.5 equiv). The mixture was stirred at room temperature for 5 hours. The mixture was directly extracted with EtOAc (500 mL) and the organic layer was washed with water (250 mL), NaHCO$_3$ saturated solution (3×250 mL) and brine (150 mL). After drying over MgSO$_4$ and concentration, the titled compound 14 (19.0 g, 40.7 mmol, 96%) was isolated as a yellow oil and was used for the next step without further purification.

Step 2d: S-cyanomethyl 2-N-acetimido-4,6-O-di-tert-butylsilylidene-3-O-[2-O-levulinoyl-3,4,6-tri-O-acetyl-β-D-galactopyranosyl]-2-deoxy-1-thio-β-D-glucopyranoside 39

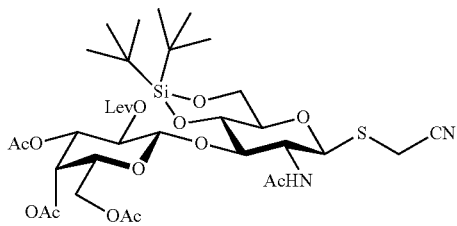

Acceptor 7 (Prepared as described in Example 1; 100 mg, 240 µmol, 1 eq) and donor 14 (168 mg, 360 µmol, 1.5 eq) were co-evaporated twice with toluene and dry under high vacuum for 1 h. DCM (2.4 mL) and MS4 Å (240 mg) were then added and the solution was stirred at r.t. for 1 h before addition of DTBMP (49 mg, 240 µmol, 1 eq) and AgOTf (142 mg, 552 µmol, 2.3 eq). The mixture was covered by aluminium foil and stirred at r.t. After 2.5 h the reaction mixture was filter over Celite and rinse with DCM. After removal of the solvent, the residue was purified by flash chromatography on silica (biotage gradient 0% to 10% EtOH in CHCl₃) and resubject to a second purification by flash chromatography on (biotage gradient 50% to 100% EtOAc in PE) to afford 39 as a white anamorphous solid (135 mg, 168 µmol, 70%).

Step 2e: S-cyanomethyl 2-N-acetimido-3-O-[2-O-levidinoyl-3,4,6-tri-O-acetyl-β-D-galactopyranosyl]-2-deoxy-1-thio-β-D-glucopyranoside 40

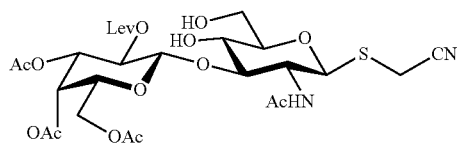

To protected 39 (1.5 g, 1.8 mmol, 1 eq) in dry THF (18 mL) at 0° C. was added NEt₃0.3HF 6530 µL, 3.8 mmol, 2.1 eq). After 1.5 h solvent were evaporated. The crude residue was purified by flash chromatography over silica (biotage gradient, 0% to 10% MeOH in EtOAc) to afford 40 as a white anamorphous solid 867.7 mg, 1.3 mmol, 72%)

Step 2f: S-cyanomethyl 2-N-acetimido-6-O-Acetyl-3-O-[2-O-levulinoyl-3,4,6-tri-O-acetyl-β-D-galactopyranosyl]-2-deoxy-1-thio-β-D-glucopyranoside 41

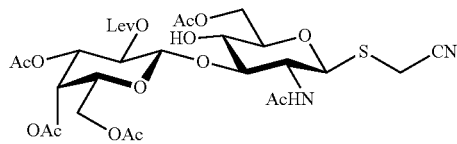

To unprotected disaccharide 40 (700 mg, 1.1 mmol, 1 eq) in dry DCM (16 mL) and dry pyridine (340 µL, 4.2 mmol, 4 eq) under argon at −78° C. was added AcCl (190 µL, 2.6 mmol, 3 eq). After 1 h methanol was added to quench the reaction and stirred a bit at −78° C. The crude was dissolve in DCM (200 mL) and washed with HCl 1N (100 mL), NaHCO₃ (100 mL), Brine (100 mL) and dried over MgSO₄. Evaporation of the solvent to dryness afford 41 as a white anamorphous solid (740 mg, 1.1 mmol, 99%)

Step 2g: S-cyanomethyl 2-N-acetimido-6-O-Acetyl-3-O-[3,4,6-tri-O-acetyl-β-D-galactopyranose]-2-deoxy-1-thio-β-D-glucopyranoside 42

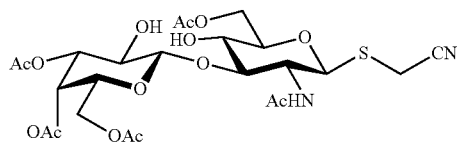

To 41 (683 mg, 1.0 mmol, 1 eq), pre-dried 30 min under high vacuum, in dry DCM (10 mL) and dry methanol (10 mL) under argon was added NH₂NH₂.AcOH (99 mg, 1.1 mmol, 1.1 eq). After 2 h more hydrazine acetate was added (10 mg, 0.1 mmol, 0.1 eq) and the reaction was stirred for another 2 h. Solvent were evaporated and the crude mixture was purified by flash chromatography on silica (biotage gradient, 0% to 10% EtOH in CHCl₃) to afford 42 as a white anamorphous solid (435 mg, 0.7 mmol, 70%)

Step 2h: S-cyanomethyl 2-N-acetamido-6-O-acetyl-4-O-[2,3,4-tri-O-p-methoxybenzyl-6-deoxy-α-L-galactopyranosyl]-3-O-[2-(2,3,4-tri-O-p-methoxy-benzyl-6-deoxy-α-L-galactopyranosyl)-3,4,6-tetra-O-acetyl-β-D-galactopyranosyl]-2-deoxy-1-thio-β-D-glucopyranoside 43

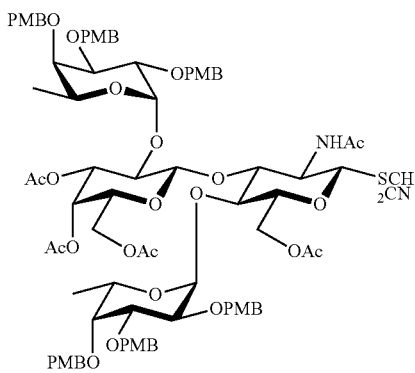

42 (300 mg, 495 µmol, 1.0 eq) and 22 (prepared in accordance with Example 1; 1125 mg, 1978 µmol, 4.0 eq) (co-evaporated 3× with toluene and dried under high vacuum for 1 h) were dissolved in dry DCM:DMF 1:1 mixture (2.0 mL) and MS4 Å (495 mg) and stirred 1 h at rt before copper(II) bromide (442 mg, 1978 µmol, 4.0 eq) and tetra-butylammonium bromide (670 mg, 1978 µmol, 2.1 eq) were added. The mixture was stirred at rt overnigth with light exclusion. The crude mixture was filtered over celite and washed with EtOAc (200 mL). The filtrate was washed with NaHCO₃ sat. aqueous solution (5×100 mL) and brine (100 mL). The aqueous layer was re-extracted with EtOAc (200 mL). The combined organic layers where dried over MgSO₄, filtered, concentrated in vacuum and purified by flash chromatography (biotage gradient, 50% to 100% EtOAc in PE) to afford 43 as a white cream foam (617 mg, 381 µmol, 77%)

Step 2i: S-cyanomethyl 2-N-acetamido-6-O-acetyl-4-O-[2,3,4-tri-O-acetyl-6-deoxy-β-L-galactopyrano-syl]-3-O-[2-(2,3,4-tri-O-acetyl-6-deoxy-β-L-galacto-pyranosyl)-3,4,6-tetra-O-acetyl-β-D-galactopyranosyl]-2-deoxy-1-thio-β-D-glucopyranoside 44

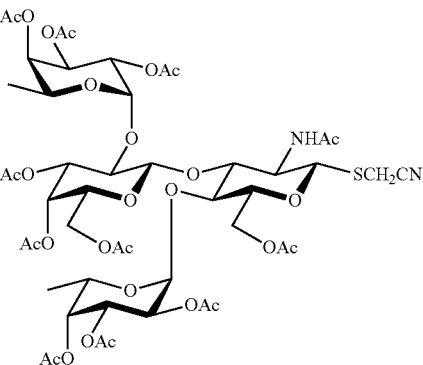

To 43 (565 mg, 349 μmol, 1.0 eq) dissolved in a mixture of MeCN:H$_2$O (9:1, 14 mL) was added CAN (2.3 g, 4.2 mmol, 12.5 eq). The solution was stirred at r.t. for 3 h before more CAN (190 mg, 347 μmol, 1.0 eq) was added. The reaction was stirred for another 4 h before acetic anhydride (26 mL), Pyridine (26 mL) and DMAP (4.3 mg, 35 μmol, 0.1 eq) were added. The mixture was stirred ON at r.t. before MeOH was added to quench the reaction. Evaporation of the solvent (with co-distillation with toluene 3 times) and direct purification by flash chromatography over silica (biotage, 70% to 100% EtOAc in PE) afford 44 as a white anamorphous solid (252 mg, 219 μmol, 63%)

Step 2j: S-cyanomethyl 2-N-acetamido-4-O-[6-deoxy-α-L-galactopyranosyl]-3-O-[2-O-[6-deoxy-α-L-galactopyranosyl]-β-D-galactopyranosyl]-2-deoxy-1-thio-β-D-glucopyranoside 24

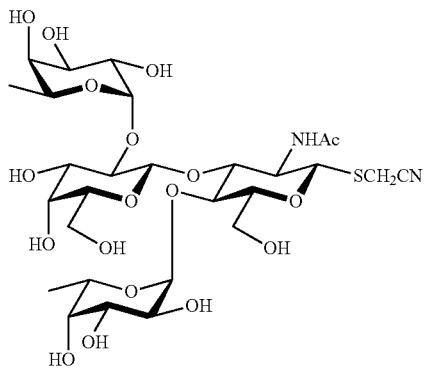

Acylated modified Le$^b$ 44 (10.0 mg, 8.37 μmol) was disolved in MeOH (83.7 μL). MeONa (25% solution, 1.913 μL) was added and the mixture was stirred for 10 min at room temperature. The reaction was quenched by introduction of ion exchange resin (Dowex, 100-200 mesh). After filtration and concentration (N$_2$ flow), the modified Le$^b$ 24 (7.7 mg, 6.5 μmol, 77%) was isolated as an amorphous white powder. $^1$H NMR (700 MHz, MeOD) δ 5.13 (d, J=3.3 Hz, 1H, H'''-1), 5.05 (d, J=4.0 Hz, 1H, H'-1), 4.82 (q, J=6.6 Hz, 1H, H''-5), 4.62 (d, J=7.2 Hz, 1H, H'-1), 4.59 (d, J=10.1 Hz, 1H, H-1), 4.34 (q, J=6.6 Hz, 1H, H'''-5), 4.08 (virt. t, J=9.6 Hz, 1H, H-3), 4.02 (virt. t, J=10.1 Hz, 1H, H-2), 3.96 (dd, J=12.4, 2.3 Hz, 1H, H-6a), 3.93 (dd, J=12.4, 3.6 Hz, 1H, H-6b), 3.87 (dd, J=10.2, 3.3 Hz, 1H, H''-3), 3.84 (d, J=17.2 Hz, 1H, SCHCN), 3.81 (dd, J=11.6, 7.5 Hz, 1H, H'-6a), 3.79 (virt. t, J=9.4 Hz, 1H, H-4), 3.77 (dd, J=10.2, 4.0 Hz, 1H, H''-2), 3.75 (br s, 1H, H''-4), 3.74-3.70 (m, 3H, H'''-2, H'''-3, H'''-4), 3.69-3.67 (m, 1H, H-6b), 3.68 (dd, J=10.1, 6.0 Hz, 1H, H'-2), 3.65 (dd, J=9.2, 3.0 Hz, 1H, H'-3), 3.62 (d, J=16.9 Hz, 1H, SCHCN), 3.47 (dt, J=9.6, 2.9 Hz, 1H, H-5), 3.47 (dd, J=7.1, 3.7 Hz, 1H, H'-5), 2.02 (s, 3H, NHAc), 1.28 (d, J=6.6 Hz, 3H, H''-6), 1.26 (d, J=6.6 Hz, 3H, H'''-6). $^{13}$C NMR (126 MHz, MeOD) δ 173.2 (NHC(=O)CH$_3$), 118.5 (CN), 102.5 (C'''-1), 101.7 (C''''-1), 99.7 (C''-1), 85.8 (C-1), 82.2 (C-5), 78.5 (C'-2), 77.8 (C-3), 76.9 (C'-3), 75.8 (C'-5), 73.8 (C''-4, C'''-4), 73.4 (C-4), 71.4 (C'''-3), 71.3 (C''-3), 70.4 (C'''-2)), 70.3 (C'-4), 70.0 (C''-2), 67.9 (C''-5), 67.3 (C'''-5), 62.9 (C'-6), 61.3 (C-6), 55.5 (C-2), 23.0 (NHC(=O)CH$_3$), 16.6 (C''-6), 16.6 (C'''-6), 15.1 (SCH$_2$CN). HRMS (m/z): calcd for C$_{28}$H$_{46}$N$_2$NaO$_{18}$S, 753.2359 ([M+Na]$^+$). Found 753.2350.

Step 2k: Mixture of S-cyanomethyl 2-N-acetamido-4-O-[6-deoxy-α-L-galactopyranosyl]-3-O-[2-O-[6-deoxy-α-L-galactopyranosyl]-β-D-galactopyranosyl]-2-deoxy-1-thio-βD-glucopyranoside 24 and S-2-imino-2-methoxyethyl 2-N-acetamido-4-O-[6-deoxy-α-L-galactopyranosyl]-3-O-[2-O-[6-deoxy-α-L-galactopyranosyl]-β-D-galactopyranosyl]-2-deoxy-1-thio-βD-glucopyranoside 46

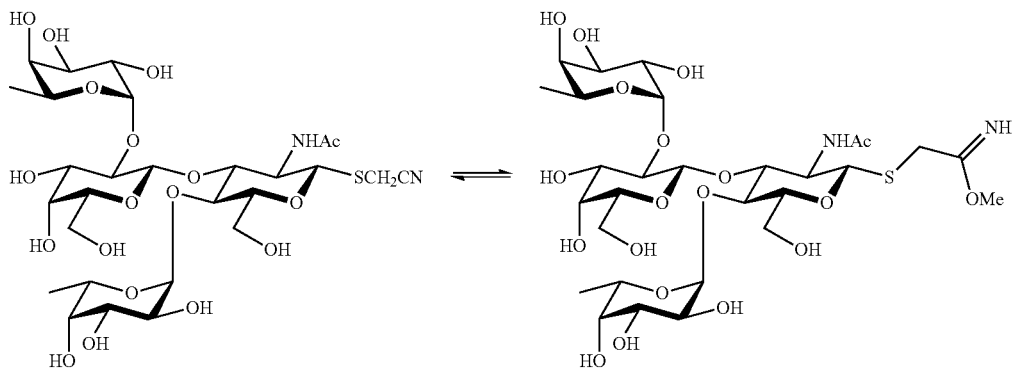

Acylated modified Le$^b$ 44 (8.8 mg, 7.3 µmol) was dissolved in anhydrous MeOH (100.5 µL) under argon. NaOMe (1M, 8.2.94 µL, 0.4 equiv) was added and the mixture was stirred for 5 d at 4° C. After concentration (N$_2$ flow for 30 min and high vacuum for 1 h), a mixture of the activated oligosaccharide S-2-imino-2-methoxyethyl 2-N-acetamido-4-O-[6-deoxy-α-L-galactopyranosyl]-3-O-[2-O-[6-deoxy-α-L-galactopyranosyl]-β-D-galactopyranosyl]-2-deoxy-1-thio-β-D-glucopyranoside 46 and of the non-activated oligosaccharide S-cyanomethyl 2-N-acetamido-4-O-[6-deoxy-α-L-galactopyranosyl]-3-O-[2-O-[6-deoxy-α-L-galactopyranosyl]-β-D-galactopyranosyl]-2-deoxy-1-thio-β-D-glucopyranoside 24 was obtained (6.1 mg, 44 mol % and 45 mass % of 46).

Example 3: Inflammation Detection

Le$^a$ and Le$^b$ were compared with alternative Lewis sugars Le$^x$ and Le$^y$ to study the efficiency of binding to the endothelium. Imaging agents comprising a conjugate of the activated Le$^a$ and Le$^b$ prepared as set out in Examples 1 and 2, and an iron oxide based imaging moiety were prepared. For comparison, corresponding imaging agents having Le$^x$ and Le$^y$ oligosaccharides were prepared in a similar manner. The procedure is set out below.

Magnetic particles were purchased from Solulink (product M-1000-001, lot ST100511). The beads were made up of a polystyrene core, surrounded with magnetite, and finally covered with a non polystyrene shell. The beads were functionalized with amino groups and had a hydrodynamic size of 732 nm, and a content of magnetite (Fe$_3$O$_4$) of 40% (supplier information).

The magnetic particles (5.8 mgFe) were washed 3 times with the reaction buffer (NaHCO$_3$ 0.1 M pH 8) using a magnet support and were suspended in 0.5 mL of reaction buffer. The mixture of activated and non activated oligosaccharides (5 to 10 equiv relative to the activated oligosaccharide) was previously solubilised in the reaction buffer (0.5 mL) and then introduced in the suspension of the magnetic particles. The mixture was shaken for 16 h at room temperature before washing the magnetic particles 3 times with MilliQ water using a magnetic support. The particles were dialyzed against MilliQ water (10 kDa MWCO), were washed 3 times with filtered (0.2 µm) MilliQ water and were suspended in filtered (0.2 µm) MilliQ water (final concentration between 4-8 mgFe/mL)

Animal Preparation

Adult male Wistar rats (Harlan-Olac, UK), weighing~250 g were anesthetized with 2.5% isoflurane in 70% N$_2$O:30% O$_2$. Using a <50 mm-tipped glass pipette, 100 ng of recombinant rat interleukin-1β (IL-1β) (NIBSC, Potters Bar, UK) in 1 µl saline was injected stereotaxically, 1 mm anterior and 3 mm lateral to Bregma, at a depth of 4 mm into the left striatum. Animals were allowed to recover from anesthesia for 2.5-3.0 h, at which point they were re-anesthetized as above and 200 W of a solution containing either (a) oligosaccharide (Le$^x$, Le$^y$, Le$^a$, Le$^b$) conjugated to 730 nm Solulink particles (4 mg Fe) prepared as set out above, or (b) non-targeted Solulink particles particles (4 mg Fe) was injected via a tail vein. In another series of experiments, a permanent middle cerebral artery occlusion was perfomed to model human stroke. Following contrast agent injection, animals were positioned in a 5 cm i.d. quadrature birdcage resonator with an in-built stereotaxic frame. During MRI, anesthesia was maintained with 1.5-1.7% isoflurane in 70% N$_2$O:30% O$_2$, ECG was monitored via subcutaneous electrodes and body temperature was maintained at ~37° C. with a circulating warm water system.

Images were acquired using a 7T horizontal bore magnet with a Brukker spectrometer. A T2*-weighted 3D gradient-echo dataset encompassing the entire brain was acquired: flip angle 11°, TR=25 ms, TE=10 ms, matrix size 350×192×192, field of view 4.2×3.07×3.07 cm, 4 averages, total acquisition time 1 h. The midpoint of the acquisition was 4.5 h after the injection and 0.5 h after. Isotropic voxel size of 88 µm. Importantly, no post-acquisition image processing was required in order to visualise the binding of the particles (lew$^a$ and lew$^b$) which appear as hypointense (black) regions in the scans.

Results are set out in Tables 1 to 4 and FIG. 1:

Table 1: 732 nm iron oxide particles from Solulink. 130-180 g rats. Injection 10 ng (1 µL) of IL-1 over 2 min.

TABLE 1

| Reference | ST100511 | GB 66a | GB 70a | GB 71a | GB 72a | GB 75a | GB 76a | GB 77a |
|---|---|---|---|---|---|---|---|---|
| Size (nm) | 734 | 734 | 734 | 734 | 734 | 734 | 734 | 734 |
| Starting material | commercial | ST100511 | ST100511 | ST100511 | ST100511 | ST100511 | ST100511 | ST100511 |
| Surface | NH$_2$ | Le$^x$ | Le$^a$ | Le$^y$ | Le$^b$ | Le$^x$ | Le$^a$ | Le$^b$ |
| Le used for synth (equiv/N) | — | 6.6 | 10 | 10 | 10 | 10 | 5 | 5 |
| NaHCO$_3$ buffer starting pH; final pH | — | 8.0; 8.8 | 8.0; 9.2 | 8.0; 9.1 | 8.0; 9.3 | 8.0; 9.2 | 8.0; 8.9 | 8.0; 9.0 |
| Le loading (Fluorescamine, % N) | | 90.8 ± 0.5 | 92.4 ± 0.4 | 88.6 ± 0.4 | 87.9 ± 0.6 | | 91.0 ± 0.4 | 87 ± 2 |
| Le loading (Fluorescamine, umol/mgFe) | | 7.79 ± 0.04 | 7.93 ± 0.03 | 7.61 ± 0.03 | 7.54 ± 0.05 | | 7.81 ± 0.03 | 7.4 ± 0.2 |
| Concentration (ICP, mgFe/mL) | 4.0-4.7 | 5.05 | 5.93 | 5.88 | 6.29 | 6.71 | 6.48 | 7.59 |
| Amout bead injected (mgFe/kg) | | 6.1 | 6.4 | 7.0 | 7.5 | 5.3 | 5.3 | 4.9 |
| Hyposignal obtained with IL-1 | | medium | high++ | medium | high | not inj | high 2/3 | high+ |

TABLE 2

| Ref experiment | Ref bead | Bead | Amount inj (mgFe/kg) | Time between IL-1 inj and inj bead inj (h) | Time between bead inj and MRI (mm) | Result |
|---|---|---|---|---|---|---|
| g_13 | GB 66-a | La-Le$^x$ | 1 | 4 | 15 | low contrast |
| g_14 | GB 66-a | La-Le$^x$ | 2 | 4 | 10 | low contrast |
| g_15 | GB 66-a | La-Le$^x$ | 4 | 4 | 10 | medium contrast |
| g_16 | Control | La | 4 | 4 | 10 | low contrast |
| g_17 | — | — | — | — | — | dead before injection |
| g_18 | GB 37-a | Sm-Lex | 4 | | 10 | low contrast |
| g_19 | GB 66-a | La-Le$^x$ | 4 | 4 | 10 | medium contrast |

TABLE 2-continued

| Ref experiment | Ref bead | Bead | Amount inj (mgFe/kg) | Time between IL-1 inj and inj bead inj (h) | Time between bead inj and MRI (mm) | Result |
|---|---|---|---|---|---|---|
| g_20 | GB 66-a | La-Le$^x$ | 4 | 4 | 10 | medium contrast |
| g_21 | Control | La | 4 | 4 | 10 | low contrast |
| g_22 | GB 66-a | La-Le$^x$ | 4 | 4 | 10 | (2 times more IL-1, same) |
| g_23 | GB 66-a | La-Le$^x$ | 4 | 3 | 90 | |
| g_24 | Control | La | 4 | 3 | 10 | |

TABLE 3

| Ref experiment | Ref bead | Bead | Injection for activation (10 ng, 1 uL) | Amount inj (mgFe/kg) | Time between IL-1 inj and inj bead inj (h) | Time between bead inj and MRI (min) | hyposignal |
|---|---|---|---|---|---|---|---|
| g_25 | GB 70a | La-Le$^a$ | IL-1 | 4 | 5 | 30 | high |
| g_26 | — | — | — | — | — | — | dead |
| g_27 | GB 71a | La-Le$^y$ | IL-1 | 4 | 4 | 15 | medium |
| g_28 | GB 70a | La-Le$^a$ | IL-1 | 4 | 4 | 15 | high |
| g_29 | GB 72a | La-Le$^b$ | IL-1 | 4 | 4 | 15 | high |
| g_30 | GB 71a | La-Le$^y$ | IL-1 | 4 | 4 | 15 | medium |
| g_31 | GB 72a | La-Le$^b$ | IL-1 | 4 | 4 | 15 | high |
| g_32 | GB 70a | La-Le$^a$ | IL-1 | 4 | 4 | 15 | high |
| g_33 | GB 37a | Sm-Le$^x$ | IL-1 | 4 | 4 | 15 | very low |
| g_34 | — | — | — | — | — | — | dead |
| g_35 | GB 72a | La-Le$^b$ | IL-1 | 4 | 4 | 15 | high |
| g_36 | — | — | — | — | — | — | dead |

TABLE 4

| Ref experiment | Ref bead | Bead | Injection for activation | Amount inj (mgFe/kg) | Time between IL-1 inj and inj bead inj (h) | Time between bead inj and MRI (min) | hyposignal |
|---|---|---|---|---|---|---|---|
| g_41 | GB 79a | La-Le$^a$ | saline ic | 4 | 4 | 15 | low |
| g_42 | GB 70a | La-Le$^a$ | saline ic | 4 | 4 | 15 | low |
| g_43 | GB 76a | La-Le$^a$ | saline ic | 4 | 4 | 15 | low |
| g_44 | GB 79a | La-Le$^a$ | TNFα | 4 | 4 | 15 | high |
| g_45 | GB 79a | La-Le$^a$ | TNFα | 4 | 4 | 15 | high |
| g_46 | GB 79a | La-Le$^a$ | TNFα | 4 | 4 | 15 | very high |
| g_47 | GB 80a | Sm-Le$^a$ | IL-1 | 2.2 | 4 | 15 | very low |
| g_48 | GB 77a | La-Le$^b$ | IL-1 | 4 | 4 | 15 | very high |
| g_49 | GB 79a | La-Le$^a$ | MCAO | 4 | 4 | 25 | medium periph |
| g_50 | GB 79a | La-Le$^a$ | MCAO | 4 | 4 | 25 | medium periph |
| g_51 | GB 79a | La-Le$^a$ | MCAO | 4 | 4 | 25 | medium periph |
| g_52 | GB 79a | La-Le$^a$ | saline iv | 4 | 4 | 15 | no signal |
| g_53 | GB 79a | La-Le$^a$ | saline iv | 4 | 4 | 15 | low signal |
| g_54 | — | — | — | — | — | — | dead |
| g_55 | — | — | — | — | — | — | dead |
| g_56 | GB 76a | La-Le$^a$ | LPS iv | 4 | 4 | 15 | high |
| g_57 | GB 79a | La-Le$^a$ | saline iv | 4 | 4 | 15 | no signal |
| g_58 | GB 79a | La-Le$^a$ | MCAO | 4 | 4 | 25 | medium periph |
| g_59 | GB 79a | La-Le$^a$ | LPS iv | 4 | 2.33 | 15 | no signal |

It can be seen from Tables 1 to 4 above that Le$^a$ and Le$^b$ provide particularly high binding, whilst Le$^x$ and Le$^y$ provide only medium binding. FIG. 1 clearly demonstrates the improvement in images obtained with Le$^a$ and Le$^b$ and the increase in binding to the activated endothelium.

The invention claimed is:
1. An imaging agent comprising a conjugate of an oligosaccharide with an imaging moiety, wherein the oligosaccharide is of formula (I) or a pharmaceutically acceptable salt or PEGylated form thereof:

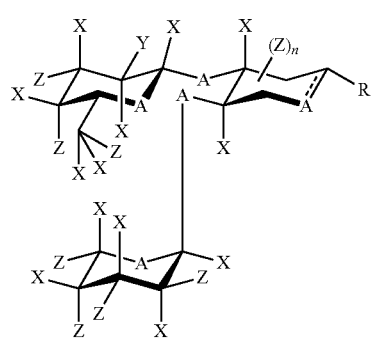

wherein each Z is the same or different and is selected from OH, hydrogen, halogen, $C_{1-6}$ alkoxy, —NR'R", —NR'COR", —N(COR')(COR"), —SR', —COR', —COOR', —OC(O)R', —OC(O)OR', —OC(O)NR'R", —OC(O)SR', —OP(O)(OR')(OR"), —OSO$_3$H, or $C_{1-12}$ alkyl, $C_{2-12}$ alkenyl or $C_{2-12}$ alkynyl, which is optionally substituted with one or more substituents selected from halogen, NH$_2$, N$_3$, CN, COOH, COO($C_{1-4}$ alkyl), OH and $C_{1-4}$ alkoxy;

each X is the same or different and is selected from OH, hydrogen, halogen, $C_{1-6}$ alkoxy, —NR'R", —NR'COR", —N(COR')(COR"), —SR', —COR', —COOR', —OC(O)R', —OC(O)OR', —OC(O)NR'R", —OC(O)SR', —OP(O)(OR')(OR"), —OSO$_3$H, or $C_{1-12}$ alkyl, $C_{2-12}$ alkenyl or $C_{2-12}$ alkynyl, which is optionally substituted with one or more substituents selected from halogen, NH$_2$, N$_3$, CN, COOH, COO($C_{1-4}$ alkyl), OH and $C_{1-4}$ alkoxy;

each A is the same or different and is selected from CR'R", O, S and NR';

n is 0, 1, 2, 3 or 4; a dotted line indicates a bond selected from a saturated bond and an unsaturated bond; Y is either a group Z as defined above or a saccharide unit of formula (II):

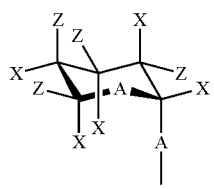

(II)

wherein X, Z and A are as defined above;
R represents the point of attachment to the imaging moiety; and
R' and R" are identical or different and are selected from hydrogen and $C_{1-12}$ alkyl groups which are optionally substituted with one or more substituents selected from halogen, NH$_2$, N$_3$, CN, COOH, COO($C_{1-4}$ alkyl), OH and $C_{1-4}$ alkoxy.

2. An imaging agent according to claim 1, wherein either all groups Z are OH, or one, two, three or four groups Z are other than OH and the remainder represent OH; either all groups X are hydrogen or one, two or three groups X are other than hydrogen and the remainder represent hydrogen; either each A is —O— or one, two or three A groups are other than —O— and the remainder represent —O—; and n is 0, 1, 2 or 3.

3. An imaging agent according to claim 1, wherein each Z is the same or different and is selected from OH, hydrogen, halogen, methoxy, ethoxy, —NH$_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio and —OP(O)(OH)$_2$.

4. An imaging agent according to claim 1, wherein each X is the same or different and is hydrogen or halogen.

5. An imaging agent according to claim 1, wherein each carbon atom that carries a group Z other than OH also carries a group X that represents OH, hydrogen, halogen, methoxy, ethoxy, —NH$_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio or —OP(O)(OH)$_2$.

6. An imaging agent according to claim 1, wherein each A is the same or different and is —O—, —SH—, —NH— or —N(Me)-.

7. An imaging agent according to claim 1, wherein the oligosaccharide is of formula (Ia) or (Ib) or a pharmaceutically acceptable salt or PEGylated form thereof:

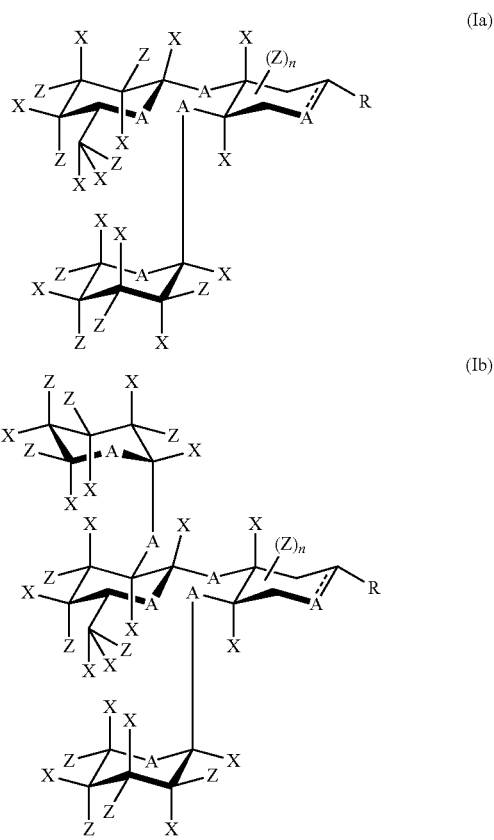

wherein:
each Z is the same or different and is selected from OH, hydrogen, halogen, methoxy, ethoxy, —NH$_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio and —OP(O)(OH)$_2$, wherein either all groups Z are OH, or one or two groups are other than OH and the remainder are OH;

each X is the same or different and is selected from hydrogen or halogen, or in the case where a group Z carried on the same carbon atom as X is other than OH, then X represents OH, hydrogen, halogen, methoxy, ethoxy, —NH$_2$, ($C_{1-2}$alkyl)amine, di($C_{1-2}$alkyl)amine, ($C_{1-2}$acetyl)amine, di($C_{1-2}$acetyl)amine, mercapto, methylthio, ethylthio or —OP(O)(OH)$_2$, wherein either all groups X are hydrogen, or one or two groups are other than hydrogen and the remainder are hydrogen;

each A is the same or different and is selected from —O—, —SH—, —NH— and —N(Me)-; wherein either all groups A are —O— or one A group is other than —O— and the remainder represent —O—;

n is 2;
the bond Cl(R)-A is saturated; and
R represents the point of attachment to the imaging moiety.

8. An imaging agent according to claim 1, wherein the oligosaccharide is Lewis A or Lewis B or a pharmaceutically acceptable salt thereof.

9. An imaging agent according to claim 1, wherein the oligosaccharide is Lewis A or a pharmaceutically acceptable salt thereof.

10. A pharmaceutical composition comprising an imaging agent as claimed in claim 1 and a pharmaceutically acceptable carrier or diluent.

11. An imaging method comprising the steps of:
(i) administering to a subject an imaging agent according to claim 1 or a pharmaceutical composition according to claim 10; and
(ii) carrying out medical imaging on the subject, wherein carrying out medical imaging comprises carrying out magnetic resonance imaging, Positron Emission Tomography or Single-Photon-Emission-Computed Tomography.

12. An imaging agent according to claim 1, wherein the contrast agent is selected from the group consisting of magnetic resonance imaging contrast agent, positron emission tomography contrast agent.

13. An imaging agent according to claim 12, wherein the magnetic resonance imaging contrast agent is selected from the group consisting of a Gd(III)-containing contrast agent, iron containing colloidal particles, and manganese containing particles.

* * * * *

UNITED STATES PATENT AND TRADEMARK OFFICE
CERTIFICATE OF CORRECTION

PATENT NO. : 10,016,518 B2
APPLICATION NO. : 14/421943
DATED : July 10, 2018
INVENTOR(S) : Daniel Anthony et al.

Page 1 of 1

It is certified that error appears in the above-identified patent and that said Letters Patent is hereby corrected as shown below:

In the Specification

Column 4, Line 27, "term alkyl(amino" should be --term di($C_{1-2}$ alkyl)amino--.

Column 7, Line 2, "-NR'COR"," should be --NR'NR", -NR'COR",--.

Column 10, Line 17, "bper is" should be --bpcr is--.

Column 10, Line 17, "(bper)" should be --(bpcr)--.

Column 22, Line 45, "µt" should be --µL--.

Column 32, Line 15, "200 W" should be --200µL--.

Signed and Sealed this
Twenty-first Day of August, 2018

Andrei Iancu
*Director of the United States Patent and Trademark Office*